US009808408B2

(12) United States Patent
Stella et al.

(10) Patent No.: US 9,808,408 B2
(45) Date of Patent: *Nov. 7, 2017

(54) BIOMARKER-BASED METHODS FOR FORMULATING COMPOSITIONS THAT IMPROVE SKIN QUALITY AND REDUCE THE VISIBLE SIGNS OF AGING IN SKIN FOR INDIVIDUALS IN A SELECTED POPULATION

(75) Inventors: Qing Stella, Cincinnati, OH (US); Karl Shiqing Wei, Mason, OH (US); Cynthia Ann Garza, Cincinnati, OH (US); Kenneth Robert Wehmeyer, Cincinnati, OH (US); Rohan Lalith Wimalasena, Mason, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 963 days.

This patent is subject to a terminal disclaimer.

(21) Appl. No.: 13/007,632

(22) Filed: Jan. 16, 2011

(65) Prior Publication Data

US 2011/0257030 A1    Oct. 20, 2011

Related U.S. Application Data

(60) Provisional application No. 61/295,732, filed on Jan. 17, 2010, provisional application No. 61/295,826, filed on Jan. 18, 2010.

(51) Int. Cl.
| | |
|---|---|
| A61Q 19/10 | (2006.01) |
| A61K 8/31 | (2006.01) |
| A61K 8/03 | (2006.01) |
| G01N 33/50 | (2006.01) |
| G01N 33/68 | (2006.01) |
| G01N 33/92 | (2006.01) |
| G06Q 30/02 | (2012.01) |

(52) U.S. Cl.
CPC ............... *A61K 8/31* (2013.01); *A61K 8/03* (2013.01); *A61Q 19/10* (2013.01); *G01N 33/5088* (2013.01); *G01N 33/6812* (2013.01); *G01N 33/6827* (2013.01); *G01N 33/6869* (2013.01); *G01N 33/6881* (2013.01); *G01N 33/92* (2013.01); *G06Q 30/0201* (2013.01); *A61K 2800/87* (2013.01); *G01N 2333/4742* (2013.01); *G01N 2333/545* (2013.01); *G01N 2500/04* (2013.01)

(58) Field of Classification Search
None
See application file for complete search history.

(56) References Cited

U.S. PATENT DOCUMENTS

| | | | |
|---|---|---|---|
| 2005/0191709 A1 | 9/2005 | Hendrix et al. | |
| 2005/0221334 A1* | 10/2005 | Benson | ............... 435/6 |
| 2005/0287088 A1* | 12/2005 | Guiramand et al. | ............. 424/59 |
| 2007/0196344 A1 | 8/2007 | Osborne et al. | |
| 2007/0202489 A1 | 8/2007 | Hendrix et al. | |
| 2007/0202490 A1 | 8/2007 | Hendrix et al. | |
| 2007/0202491 A1 | 8/2007 | Hendrix et al. | |
| 2007/0224696 A1 | 9/2007 | Honkonen et al. | |
| 2009/0324521 A1 | 12/2009 | Cetti et al. | |
| 2010/0105102 A1* | 4/2010 | Hanes | ............... A61B 10/02 435/29 |
| 2010/0190675 A1 | 7/2010 | Cetti et al. | |
| 2011/0033842 A1* | 2/2011 | Moon | ............... A61B 10/02 435/5 |
| 2011/0071123 A1 | 3/2011 | Schwartz et al. | |
| 2011/0162668 A1 | 7/2011 | Coffindaffer et al. | |
| 2011/0165607 A1 | 7/2011 | Takeda et al. | |
| 2011/0247954 A1 | 10/2011 | Wei | |
| 2011/0250141 A1 | 10/2011 | Wei | |
| 2011/0251872 A1 | 10/2011 | Wei | |
| 2011/0253157 A1 | 10/2011 | Wei | |
| 2011/0253158 A1 | 10/2011 | Wei | |
| 2011/0257020 A1 | 10/2011 | Stella et al. | |
| 2011/0262025 A1 | 10/2011 | Jarrold et al. | |
| 2011/0262570 A1 | 10/2011 | Finlay et al. | |
| 2017/0049673 A1 | 2/2017 | Wei | |

FOREIGN PATENT DOCUMENTS

| | | |
|---|---|---|
| JP | 10-216106 A | 8/1998 |
| WO | WO 2007/129330 A1 | 11/2007 |
| WO | WO 2007/129331 A2 | 11/2007 |
| WO | WO 2008/066612 A2 | 6/2008 |
| WO | WO 2009/073382 A2 | 6/2009 |

(Continued)

OTHER PUBLICATIONS

Becker et al., Detection of Differentially Regulated Genes in Keratinocytes by cDNA Array Hybridization: Hsp27 and Other Novel Players in Response to Artificial Ultraviolet Radiation, Journal of Investigative Dermatology, vol. 116, No. 6, Jun. 2001, pp. 983-988.

Ertel et al., Leg wash protocol to assess the skin moisturization potential of personal cleansing products, International Journal of Cosmetic Science, vol. 21, No. 6 Dec. 1999, pp. 383-397.

Grando et al., Adrenergic and Cholinergic Control in the Biology of Epidermis: Physiological and Clinical Significance, Journal of Investigative Dermatology vol. 126, pp. 1948-1965 (2006).

International Search Report and Written Opinion of the International Searching Authority PCT/US2010/040077 dated Nov. 30, 2010, 18 pages.

(Continued)

*Primary Examiner* — Christopher M Gross

(57) ABSTRACT

In various embodiments, provided are methods for selecting and formulating compositions for treating and maintaining the quality of skin in a select population, wherein a composition is selected for use in a personal care product based on its demonstrated biological effect to improve skin quality in the population as evidenced by one or more biomarker changes that correlate with improvement as evidenced by one or more objective measurements of skin health in the population.

6 Claims, 24 Drawing Sheets

(56) References Cited

FOREIGN PATENT DOCUMENTS

| WO | WO 2009/077995 A1 | 6/2009 |
| --- | --- | --- |
| WO | WO 2009/081374 A2 | 7/2009 |
| WO | WO 2010/088429 A2 | 8/2010 |
| WO | WO 2010/088430 A2 | 8/2010 |
| WO | WO 2010/088432 A2 | 8/2010 |
| WO | WO 2010/101685 A2 | 9/2010 |
| WO | WO 2011/087523 A1 | 7/2011 |
| WO | WO 2012/009298 A2 | 1/2012 |

OTHER PUBLICATIONS

International Search Report and Written Opinion of the International Searching Authority PCT/US2010/040074 dated Jan. 21, 2011, 18 pages.

International Search Report and Written Opinion of the International Searching Authority PCT/US2010/040075 dated Dec. 1, 2010, 22 pages.

Kikuchi et al., Improvement of Mild Inflammatory Changes of the Facial Skin Induced by Winter Environment with Daily Applications of a Moisturizing Cream. A Half-Side Test of Biophysical Skin Parameters, Cytokine Expression Pattern and the Formation of Cornified Envelope, Dermatology, vol. 207, No. 3, 2003, pp. 269-275.

Marzatico et al., Evaluation of anti-wrinkle, elasticizing, ridensifying and skin barrier "repairing" efficacy of a cosmetic treatment, Farcoderm Tested Wellness, BIOTIVIA, Jun. 18, 2009, 42 pages.

Schallreuter et al., The induction of the $\alpha$-1-adrenoreceptor signal transduction system on human melanocytes, Experimental Dermatology 1996; vol. 5, Issue 1, pp. 20-23.

Voegeli et al., Efficient and simple quantification of stratum corneum proteins on tape strippings by infrared densitometry, Skin Research and Technology 2007; 13; 242-251.

\* cited by examiner

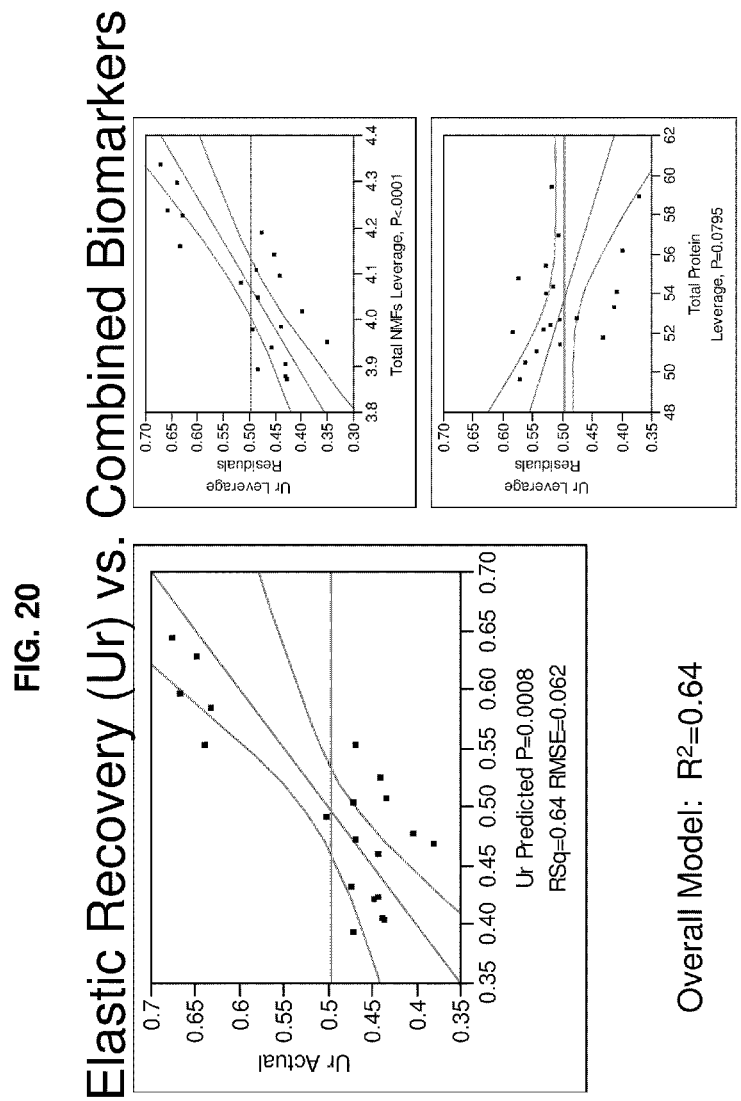

Dryness vs. Combined Biomarkers

Dryness vs. Combined Biomarkers

BIOMARKER-BASED METHODS FOR FORMULATING COMPOSITIONS THAT IMPROVE SKIN QUALITY AND REDUCE THE VISIBLE SIGNS OF AGING IN SKIN FOR INDIVIDUALS IN A SELECTED POPULATION

CROSS REFERENCE TO RELATED APPLICATIONS

This application claims the benefit of U.S. Provisional Application Ser. Nos. 61/295,732 filed Jan. 17, 2010, and 61/295,826 filed Jan. 18, 2010.

FIELD

The present disclosure relates to methods for identifying compositions that can improve the health of epithelial tissue. It also relates to the use of such materials selected by such methods, for formulating and preparing at least one personal care composition.

BACKGROUND

The signs of skin damage and aging include, but are not limited to, outward visibly and tactilely perceptible changes that include but are not limited to: textural discontinuities such as wrinkles and coarse deep wrinkles, fine lines, crevices, bumps, large pores, unevenness, roughness, sagging, puffiness; blotchiness and sallowness; hyperpigmentation, including discoloration, spots and freckles; keratoses, abnormal differentiation, hyperkeratinization, elastosis, and collagen breakdown; and loss of one or more of elasticity, firmness, tightness, and recoil from deformation. Such signs may be caused or induced by factors that are intrinsic to the aging body, or are extrinsic, such as environmental damage. Skin damage and aging involves one or more layers of epithelial tissue, and is often most evident in the stratum corneum, the outermost layer of skin, though damage and changes may present in any of the layers of the epithelia/epidermis, dermis, underlying tissues and vasculature.

The consumer products and cosmetics industries are focused, at least in part, on providing products to consumers that reduce the signs of skin damage and aging. Such products may be exclusively designed to improve the appearance of skin, though many include one or more other functional benefits, such as cleansing, delivery of color, texture or scent, and exfoliation, to name a few. To date, little scientific data exists to demonstrate whether and how cosmetics and other products influence the quality or health of skin. Indeed, most products do little more than coat and temporarily moisturize or soften the stratum corneum, and these benefits are transient and superficial. In recent years, basic scientific research and applied pharmaceutical research has expanded the understanding of the biochemical processes that underlie tissue damage and tissue aging, including skin. This developing scientific knowledge has influenced both the cosmetics and personal care products industries, and its influence is evident in the contexts of cleansing and other personal care products as well as cosmetics.

In recent years, consumers have been presented with a panoply of products that purport to provide scientifically-based solutions to skin aging by providing actives with antioxidant, anti-inflammatory and free-radical-scavenging effects, to name a few. Yet it remains the case with many products that the actual cellular and physiological effects on consumers, when measured against objective standards, are lacking, though the actives may exhibit the claimed properties in the laboratory. Moreover, there is a distinct lack of evidence regarding how and in what doses product actives, whether new or old, impact the quality and health of skin. This lack of clinical understanding inherently limits effective formulation of products and delivery regimens that confer actual improvement to skin tissues and cells.

The present inventors recognized the disconnects between the skin science and the existing knowledge about skin care products.

SUMMARY

Accordingly, it is an objective of the present invention to apply the basic science knowledge about biomarkers and skin health in a rigorous and objective manner to identify and evaluate test agents for usefulness in personal care products to improve skin health. Methods are provided which enable identification and characterization of agents which positively influence cellular and tissue properties to maintain or restore health to the skin. Representative compositions are described which are tested and positively identified as influencing statically significant changes in a variety of skin biomarkers. These biomarker changes are shown to correlate closely with objective measures of improved skin health. A representative panel of biomarkers includes inflammatory cytokines, natural moisturizing factors, keratin 1, keratin 10, keratin 11, lipids and total protein.

These and other features, aspects, and advantages of the embodiments disclosed herein will become evident to those skilled in the art from a reading of the present disclosure with the appended claims.

BRIEF DESCRIPTION OF THE DRAWINGS

FIG. 20 shows plots of objective physical measurement of elastic recovery improvement as a function of combined biomarker measurements.

DETAILED DESCRIPTION

The present invention is based in part of discovery by the inventors that beneficial effects of consumer personal care products can be detected within the tissue and cells using one or more tissue and cellular biomarkers. The inventors identified and characterized a panel of biomarkers that demonstrate statistically significant changes within skin tissue in response to treatment with test agents. In many instances, these changes have been demonstrated by the inventors to closely correlate with objective measures of skin health. As a result of the inventors' efforts, the invention provides in some embodiments a panel of biomarkers, one or more of which can be used as an indicator of positive benefits of one or more test agents on skin. In some aspects, the invention also includes specific correlations between one or more of the biomarkers and one or more objective measures of skin health. Therefore, use of the biomarker panels enables the efficient screening and identification of test agents as providing one or more beneficial effects for use in any of a variety of formulations for consumer use.

It will be appreciated by one of skill in the art that a test composition which demonstrates beneficial effects based on biomarker measurement may be useful in cosmetic and other personal care products, including leave-on and rinse-off formulations. Since rinse-off compositions are not left on the skin to provide continued delivery of benefit agents, it is an especially great challenge in the art to provide rinse-off products that have beneficial effects that persist after the product is rinsed away. As described herein in particular detail in the examples, the screening methods are ideal for formulating rinse-off products which are typically contacted with a consumer's skin for only a brief time.

Figure 1:
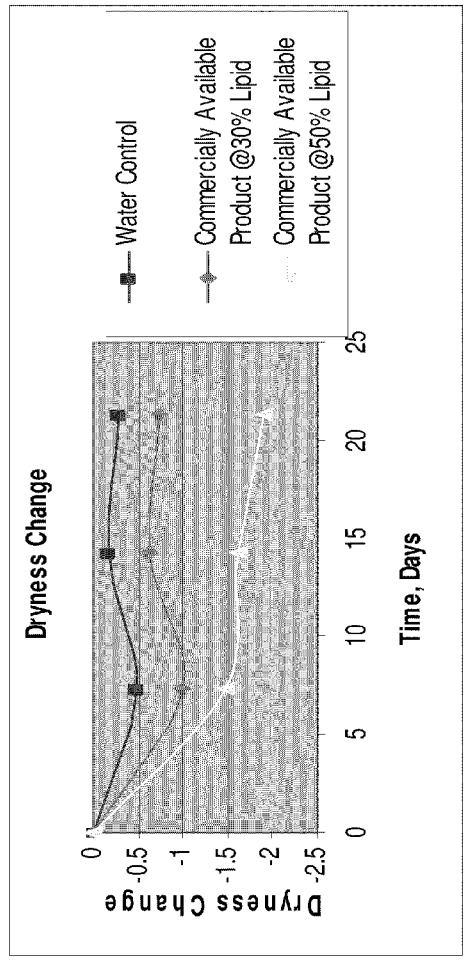
FIG. 1 shows representative results with two different constant lipid products (commercially available) wherein the products provide varying skin conditioning when delivered over a time period of 21 days, with measurements taken for dryness change at days 7, 14 and 21.

It is known that skin quality is not maintained during sporadic treatment with rinse-off compositions, generally. And it is known that skin quality is not maintained or even improved using rinse-off compositions that comprise relatively low hydrophobic benefit phase, for example compositions comprising ratios of lathering phase to hydrophobic benefit phase that are in the range from more than 90:10 to about 60:40 (by weight). FIG. 1 shows representative results with two different constant lipid products (commercially available) wherein the products provide varying skin conditioning when delivered over a time period of 21 days, with measurements taken for dryness change at days 7, 14 and 21. Referring again to FIG. 1, only the 50% lipid shows a significant sustained benefit with continued use as compared with water. In contrast, the 30% lipid shows only a modest improvement over time as compared with water.

These results together with the results described in the Examples herein below show that the measured improvement in skin quality conferred during the treatment stage (the period of delivery of a hydrophobic benefit phase in a rinse-off product) persists well beyond the cessation of treatment. These results were unexpected. Even more unexpected were the results as described herein relating to the positive change in various biomarkers associated with treatment with hydrophobic benefit phase and the correlation of those positive changes with measured physical properties of skin. Notably, these results are particularly surprising since the tested skin was not classified as diseased.

Accordingly, developed in accordance with the methods described herein, the test formulations include compositions that are selected for their demonstrable ability to enhance skin health. Most moisturizing body washes are designed to address dryness using surface moisturizers, but this is only a temporary fix for dry skin. Personal care compositions such as body washes, formulated in accordance with the inventive methods provide benefits beyond moisturizing skin at the surface and demonstrably penetrate the skin to improve overall skin health at the cellular level, as evidenced by changes in molecular biomarkers that correlate with objective measures of skin health. This is an advancement over the art, and surprisingly enables provision of specially formulated compositions and treatment regimens.

I. DEFINITIONS

"Biomarker" as used herein refers to any biological molecules (genes, proteins, lipids, metabolites) that, singularly or collectively, reflect the current or predict future state of a biological system. Thus, as used herein, various biomarkers are indicators of the quality of skin in terms of elasticity including elastic extension and elastic recovery, firmness, tissue hydration, brightness, tone, smoothness, appearance of lines, visual properties of dryness and condition, sagging, the presence of flaking, cohesiveness as evidenced by total protein, lipid content, and trans-epidermal water loss. Non-limiting examples of biomarkers include inflammatory cytokines, natural moisturizing factors, one or more of keratins 1, 10 and 11, lipids and total protein. The response of skin to treatment with personal care compositions can also be assessed by measuring one or more biomarkers.

"Comprising" as used herein is inclusive and does not exclude additional, unrecited elements, steps or methods. Terms as used herein that are synonymous with "comprising" include "including," "containing," and "characterized by," and mean that other steps and other ingredients can be included. The term "comprising" encompasses the terms "consisting of" and "consisting essentially of," wherein these latter terms are exclusive and are limited in that additional, unrecited elements, steps or methods ingredients may be excluded. The personal cleansing compositions and methods of the present disclosure can comprise, consist of, or consist essentially of, the elements, steps and methods as described herein.

"Consumer" as used herein refers to an individual who purchases and/or uses compositions in accordance with the disclosure. In some instances, therefore, a consumer may be alternately referred to herein as a "user."

"Control surfaces" as used herein means a region of epithelial tissue which has not been contacted with and/or by the product, such as a consumer product and/or a test product, which has contacted the affected surface. Typically, control surface is will be of similar epithelial tissue which has not contacted the product. Alternatively, the control surface may be the same epithelial tissue as the affected surface. In this case the control surface is harvested some time prior, such as from 1 second to 5 or 6 weeks or possibly even longer to the application of the test product and/or comparison product to the epithelial tissue, which is then harvested to collect the test sample.

"Effective amount" as used herein means an amount of a compound or composition sufficient to significantly induce a positive skin benefit, including independently or in combination with other benefits disclosed herein. This means that the content and/or concentration of active component in the formulation is sufficient that when the formulation is applied with normal frequency and in a normal amount, the formulation can result in the treatment of one or more undesired skin conditions (e.g., skin wrinkles). For instance, the amount can be an amount sufficient to inhibit or enhance some biochemical function occurring within the skin. This amount of active component may vary depending upon, among other factors, the type of product and the type of skin condition to be addressed.

"Epidermis" as used herein refers to the outer layer of skin, and is divided into five strata, which include the: stratum corneum, stratum granulosum, stratum spinosum, and stratum basale. The stratum corneum contains many layers of dead, anucleated keratinocytes that are essentially filled with keratin. The outermost layers of the stratum corneum are constantly shed, even in healthy skin. The stratum lucidum contains two to three layers of anucleated cells. The stratum granulosum contains two to four layers of cells that are held together by desmosomes that contain keratohyaline granules. The stratum spinosum contains eight to ten layers of modestly active dividing cells that are also held together by desmosomes. The stratum basale contains a single layer of columnar cells that actively divide by mitosis and provide the cells that are destined to migrate through the upper epidermal layers to the stratum corneum. Thus, the predominant cell type of the epidermis is the keratinocyte. These cells are formed in the basal layer and exist through the epidermal strata to the granular layer at which they transform into the cells know as corneocytes or squames that form the stratum corneum. During this transformation process, the nucleus is digested, the cytoplasm disappears, the lipids are released into the intercellular space, keratin intermediate filaments aggregate to form microfibrils, and the cell membrane is replaced by a cell envelope made of cross-linked protein with lipids covalently attached to its surface. Thus, keratins are the major structural proteins of the stratum corneum. Corneocytes regularly slough off (a process known as desquamation) to complete an overall process that takes about a month in healthy human skin. In stratum corneum that is desquamating at its normal rate, corneocytes persist in the stratum corneum for approximately 2 weeks before being shed into the environment.

"Epithelial tissue" as used herein refers to all or any portion of the epithelia, in particular the epidermis, and includes one or more portions of epithelia that may be obtained from a subject by a harvesting technique known in the art, including those described herein. By way of example and without being limiting, epithelial tissue refers to cellular fragments and debris, proteins, isolated cells from the epithelia including harvested and cultured cells. Some non-limiting examples of sources of epithelial tissue include, skin on the face, head, torso and limbs of a subject.

"Hydrophobic benefit phase" as used herein, refers to the composition that comprises one or a combination of hydrophobic benefit materials that deliver one or more benefits including skin conditioning, skin moisturization, and skin health benefits. The term "lipid" is used herein in reference to hydrophobic benefit phases. In accordance with some embodiments, hydrophobic benefit phases are selected from the group consisting of petrolatum, lanolin, derivatives of lanolin (non-limiting examples include lanolin oil, isopropyl lanolate, acetylated lanolin, acetylated lanolin alcohols, lanolin alcohol linoleate, lanolin alcohol riconoleate) hydrocarbon oils (e.g. mineral oil) natural and synthetic waxes (non-limiting examples include micro-crystalline waxes, paraffins, ozokerite, lanolin wax, lanolin alcohols, lanolin fatty acids, polyethylene, polybutene, polydecene, pentahydrosqualene) volatile or non-volatile organosiloxanes and their derivatives (non-limiting examples include dimethicones, cyclomethicones, alkyl siloxanes, polymethylsiloxanes, methylphenylpolysiloxanes), natural and synthetic triglycerides (non-limiting examples include castor oil, soy bean oil, sunflower seed oil, maleated soy bean oil, safflower oil, cotton seed oil, corn oil, walnut oil, peanut oil, olive oil, cod liver oil, almond oil, avocado oil, palm oil, sesame oil), and combinations thereof.

"Lathering phase" as used herein refers to the composition that comprises a surfactant, which when combined with water and mechanically agitated generates a foam or lather sufficient to cause a personal care composition to provide a lather, and which, when tested using the Total Lather Volume Method disclosed herein, yield lather volumes in the range from 800 ml to more than 1500 ml.

"Package" includes any suitable container for personal care compositions.

"Personal care article" as used herein, refers to a delivery means (such as a "Package") comprising a "personal care composition."

"Personal care composition" as used herein, refers to compositions intended for topical application to the epithelia, including skin and hair. The compositions used in accordance with the present disclosure include topically applied compositions, including leave-on formulations, and rinse-off formulations in which the product is applied topically to the skin or hair and then is subsequently rinsed within minutes from the skin or hair with water, or otherwise wiped off using a substrate with deposition of a portion of the composition. Such rinse off compositions may be used as body washes, moisturizing body wash, shampoo, conditioning shampoo, hair conditioner, shower gels, skin cleansers, cleansing milks, hair and body wash, in shower body moisturizer, pet shampoo, shaving preparations and cleansing compositions used in conjunction with or applied to a disposable cleansing cloth and other types of products. The personal care composition used in accordance with the present disclosure is typically dispensible from a package. Thus, in some embodiments, the dispensing may be by extruding. In some embodiments the package may be a single chamber package, or a multi chamber package, or a set of discrete packages. The personal care compositions used in accordance with the present disclosure can be in the form of liquid, semi-liquid, cream, lotion or gel compositions intended for topical application to skin.

"Premium experience stage" refers to stages in which the components in a personal care composition are associated with delivery of one or more experiential benefits to the user at the time of use, such as lathering and delivery of scent for excellent in-use characteristics during cleansing process. The term "Conditioning Stage" refers to stages in which the components in a personal care composition are associated with delivery of one or more benefits during use, for example, deposition of hydrophobic benefit phase on the skin, that provide long term benefits after use.

"Sagging" as used herein means the laxity, slackness, or the like condition of skin that occurs as a result of loss of, damage to, alterations to, and/or abnormalities in dermal elastin, muscle and/or subcutaneous fat.

"Signs of aging" include, but are not limited to, all outward visibly and tactilely perceptible manifestations as well as any other macro or micro effects due to skin aging. Such signs may be induced or caused by intrinsic factors or extrinsic factors (such as chronological aging and/or environmental damage). These signs may result from processes which include, but are not limited to, the development of textural discontinuities such as wrinkles and coarse deep wrinkles, fine lines, skin lines, crevices, bumps, large pores (e.g., associated with adnexal structures such as sweat gland ducts, sebaceous glands, or hair follicles), or unevenness or roughness, loss of skin elasticity (loss and/or inactivation of functional skin elastin), sagging (including puffiness in the eye area and jowls), loss of skin firmness, loss of skin tightness, loss of skin recoil from deformation, discoloration (including undereye circles), blotching, sallowness, hyperpigmented skin regions such as age spots and freckles, keratoses, abnormal differentiation, hyperkeratinization, elastosis, collagen breakdown, and other histological changes in the stratum corneum, dermis, epidermis, the skin vascular system (e.g., telangiectasia or spider vessels), and underlying tissues (e.g., fat and/or muscle), especially those proximate to the skin.

"Skin" is divided into two main structural layers, the outer epidermis and the inner dermis, and as used herein, refers to the portion of the skin that comprises keratin-containing layers of epithelial tissue disposed as the epidermis of mammals (e.g., humans, dogs, cats, etc.) which includes, but is not limited to, skin, mucosa, lips, hair, toenails, fingernails, cuticles, hooves, etc.

"Stage" as used herein refers to a distinguishable part in a cycle of treatment or application of a personal care product according to the disclosure herein. For purposes hereof, a stage need not be limited to a particular period of time. Stages are distinct from one another in that the properties, most particularly the ratio of lathering phase to hydrophobic benefit phase, of a personal care composition vary between sequential stages. Thus, in a cycle comprising three stages of treatment or application, each stage may involve use of personal care compositions that vary relative to one another, for example wherein the ratio of lathering phase to hydrophobic benefit phase varies between each of the stages. In another example, in a cycle comprising three stages of treatment or application, two of the stages may involve use of personal care compositions that do not vary relative to one another while a third stage varies from the other two. In yet another example in a cycle comprising two stages of treatment or application, each stage may involve use of personal care compositions that vary relative to one another, for example wherein the ratio of lathering phase to hydrophobic benefit phase varies between each of the stages.

"Stratum corneum" as used herein, refers to the outermost layer of the epithelia, or the epidermis, and is the skin structure that provides a chemical and physical barrier between the body of an animal and the environment. The stratum corneum is a densely packed structure comprising an intracellular fibrous matrix that is hydrophilic and able to trap and retain water. The intercellular space is filled with lipids formed and secreted by keratinocytes and which provide a diffusion pathway to channel substances with low solubility in water. A commonly espoused skin metaphor portrays the stratum corneum as a brick wall wherein each brick is a corneocyte and the intercellular matrix is the mortar.

"Subject" as used herein refers to an animal, such as a human, for whom product or composition is tested or on whom a product or composition is used in accordance with the methods described herein.

"Surfactant" as used herein means the total of all anionic, nonionic, amphoteric, zwitterionic and cationic surfactants in a phase, and is also referred to as a "lathering phase" herein. When calculations are based on the surfactant, water and electrolyte are excluded from the calculations involving the surfactant, since surfactants as manufactured typically are diluted and neutralized.

"Test compositions" and "test agents" as used herein include and encompass purified or substantially pure compounds, as well as formulations comprising one or multiple compounds, and commercially available products. Thus, non-limiting examples of test compositions include water, a pharmaceutical or cosmeceutical, a product, a mixture of compounds or products, and other examples and combinations and dilutions thereof.

"Test surfaces" as used herein means a region of epithelia tissue which has been contacted with and/or by a product, such as a consumer product and/or a test product or composition, whereby the contact of the product on the epithelia tissue has resulted in some change, such as but not limited to, physiological, biochemical, visible, and/or tactile changes, in and/or on the epithelia tissue that may be positive or negative. In some examples, positive effects caused by product may include but are not limited to, reduction in one or more of erythema, trans-epidermal water loss (TEWL), discoloration of the skin, rash, dermatitis, inflammation, eczema, dandruff, edema and the like. The location of the affected surface will depend upon the product used or the location of some physiological, biochemical, visible, and/or tactile change in and/or on the epithelia tissue. For example, in the case of a body wash the test surface would typically include skin on the torso or appendages, and in the case of shampoo the test surface would typically include the head/scalp, and in the case of shaving aids, the test surface would typically include the face, underarms, or legs.

"Topical application", "topically", and "topical", as used herein, mean to apply (e.g., spread, spray) the compositions used in accordance with the present disclosure onto the surface of the skin.

"Treating" or "treatment" or "treat" as used herein includes regulating and/or immediately improving skin cosmetic appearance and/or feel.

II. FORMULATING SKIN CARE COMPOSITIONS THAT IMPROVE SKIN HEALTH

As more fully described herein below, provided are methods for formulating skin care compositions based on the use of biomarker panels for assessing the effects of test agents on skin health. In the course of formulating personal care compositions for the skin, selection of the actives and other composition components may be guided by the application of the biomarkers that are shown herein to be reflective of skin health. Thus, in various embodiments, measurement of skin response to test agents provides information about the biological effects of the test agents on skin. As further described herein, positive biomarker results correlate well with objective physical measurements of skin health. Thus the biomarker panel analysis described herein can be predictive of the ultimate benefit of an active in a skin care composition.

Evaluating Changes in Epithelial Tissue: Biomarkers

In some embodiments, methods are provided for evaluating changes on one or more surfaces of epithelial tissue of a subject caused by a test product. The methods include measuring one or more of biomarkers that are indicative of tissue health. In some embodiments, the methods also include measuring one or more of physical properties that are indicative of tissue health. The methods allow for a relatively simple, efficient and quick determination of the usefulness of a test product for providing one or more benefits to skin.

Obtaining Epithelial Tissue Samples

In accordance with some embodiments, the methods of the present involve obtaining samples of epithelial tissue to collect and analyze biomarker analytes. Any method suitable for obtaining epithelial tissue may be used, provided that the method obtains one or more of cellular debris, secretions from the epithelial tissue, and cells. Non-limiting examples of suitable obtaining techniques include, application of tape, rinsing by lavage method, biopsy, swabbing, scraping, blotting and combinations thereof. However, whichever obtaining technique is used, it must be one where the biomarkers obtained are those present on the surface, and/or in the epithelial tissue and not include any of the underlying non-epithelial tissue, such as muscle.

One suitable method of obtaining epithelial tissue is by application of tape, such as but not limited to, any type of medical tape. This technique is well known in the art and is relatively simple to implement. The technique involves application of a tape to the epithelial tissue, typically skin, which is then removed therefrom. The biomarker analytes obtained from the epithelial tissue and present on the tape are then removed from the tape in any fashion that preserves the biomarker analytes for suitable detection and measurement assays. Provided herein below are examples describing tape strip analyses. Exemplary tapes include, but are not limited to: D-squame Tape®, and SEBUTAPE®, both of which are available from CuDerm Corporation, Dallas, Tex., USA; and Transpore® tape which is available from the 3M company, of Minnesota USA.

It will be appreciated that other methods of obtaining samples of epithelial tissue may be used, and can include not only tissue obtained from a subject, but also tissue that is cultured, such as live cells.

Biomarker Analytes

Biomarker analytes are present in the test and control samples and are identified using one or more of the techniques known in the art, examples of which are described herein in the examples. In some non-limiting examples, biomarker analytes include inflammatory cytokines, natural moisturizing factors (NMFs), keratin 1, keratin 10, keratin 11, lipids and total protein. Examples of inflammatory cytokines include IL1r α and IL 1α. Examples of NMFs include amino acids, lactic acid, urea, and pyrrolidone carboxylic acid, and more particularly include Trans-Urocanic Acid, Citrulline, Glycine, Histidine, Ornithine, Proline, 2 Pyrrolidone 5 Acid, and Serine. Examples of lipids include: ceramides, including for example, NP-C18, NP-C23, NP-C26, NP-C28, NP-C30, AP-C24, AP-C26, AH-C24, AH-C26, NdS-C24, NdS-C26, EOS-C30; fatty acids, including for example C16:0, C16:1, C18:0, C18:1, C18:2; Trans-Urocanic Acid; Citrulline; Glycine; Histidine; Ornithine; Proline; 2 Pyrrolidone 5 Acid; and Serine.

The number and type of biomarker analytes detected and measured in accordance with the provided methods therefore include these non-limiting examples of biomarker analytes: alpha-actinin; alpha-catenin; actin; actin binding proteins; catenins; cytokeratins type I; cytokeratins type II; skin chymotrypsin-like enzymes; cytokeratins type I; cytokeratins type II; Desmogelin 1 and other desmogleins; fibronectin and fibronectin associating proteins; hyaluronic acid; involucrin; integrins; intercellular adhesion molecules; human serum albumin; E-cadherin and classical family members such, as but not limited to, desmocollin; profillagrin and its break down products including, but not limited to, natural moisturization factor and the amino acids from it; cellular retinoid binding proteins; ceramides; Cholesterol and biological modifications of cholesterol including, but not limited to, hormones such as cortisol and testosterone;

proteoglycans including heparan and chondroitin-6 sulfate; keratin associated proteins; loricrin; trichohyalin; Collagen, such as but not limited to, collagens of the basement membrane such as, but not limited to, collagens I, III and IV, and collagen-associated proteins such as, but not limited to, nidogen and laminin; collagenases; cornifin; calcium binding proteins, such as but not limited to S100; desmocollins; desmogleins; desmoplakin; keratohyalin; sphingolipids; total disulfide bond content for the concentration within the sample of cysteine cross-links; inositol containing compounds; melanization signal pathways including, but not limited to, alpha-MSH, microtubules composed of tubulin and associated proteins including, but not limited to, microtubule associated protein one (MAP1) and the like; intermediate filaments such as, but not limited to, the keratins, lamins, and vimentin and associated proteins such as but not limited to, plakoglobin; kalinin; plectin; keratohyalin granules and the proteins contained within them; laminin; lipids; lipoproteins; nidogen; pancornulins; cornifin; keratolinin; profilin; cross-linking cell envelope proteins; envelope precursor proteins; retinoic acid binding proteins; SPARC; small proline rich proteins (SPRR) including, but not limited to, SPRR1, 3, and 4; spectrin and spectrin-like proteins; talin; keratinocyte transglutaminase-1 and other soluble transglutaminases; syndecan; tenascin; tensin; trichohyalin; triglycerides; tubulin; tyrosinases and their enzymatic products; vimentin; vinculin; cellular division markers such as, but not limited to, cyclins and cyclin dependent kinases; diffipoptosis (differentiation) markers such as but not limited to, caspase 14; and apoptosis markers and indicators such as, but not limited to, bax and bcl-2; alpha-melanocyte stimulatory hormone; arachidonic acid and its metabolites such as, but not limited to, thromboxane, prostaglandins, and leucotreines; basic fibroblastic growth factor; vitamins; minerals (esp. Zinc, Calcium, Magnesium, etc.); cytokines and chemokines; epithelial growth factors; retinoic acid; sebocyte products; and eccrine gland products and the like.

Detection and Measurement of Biomarker Analytes

According to various embodiments, biomarker analytes are identified using any of a variety of techniques known in the art for detection, including methods known in the art and described herein below for detection of biomarkers that include but are not limited to inflammatory cytokines, natural moisturizing factors, keratin 1, keratin 10, keratin 11, lipids and total protein. Thus, in various embodiments, detection techniques such as antibodies, nucleotide probes, highly specific chemical tags, markers, dyes, enzyme linked and other colorimetric and fluorometric probes and assays can be used to detect and measure biomarker analytes. Kits and reagents as well as published techniques for biomarker detection and measurement are well known in the art.

Biomarker Panels

As described herein, a variety of biomarkers can be analyzed to assess the effects of one or more test agents on skin. Accordingly, in various embodiments, biomarker panels may comprise one, two or more different biomarkers. Representative examples of biomarker analyses and various panels of biomarkers are described herein in the examples section. As described herein, a variety of agents were tested for their effects on skin health, and biomarker panel testing results were analyzed for correlation with skin health measurements. In some examples, test compositions including glycerin emulsions, water emulsions and alternative lipid additives were tested and demonstrated significant biomarker changes in total protein, lipids and cytokines. In other examples, test compositions with fixed components in which lipid content was either varied or held constant demonstrated significant biomarker changes that evidenced persistent benefit beyond the treatment period.

These are the first known reports of cellular responses to skin care products. In particular, the results herein are the first known report showing statistically significant increases in skin lipids and reduction of inflammatory cytokines using rinse-off body care products. These results are particularly surprising since the tested skin was not classified as diseased.

Figure 4:
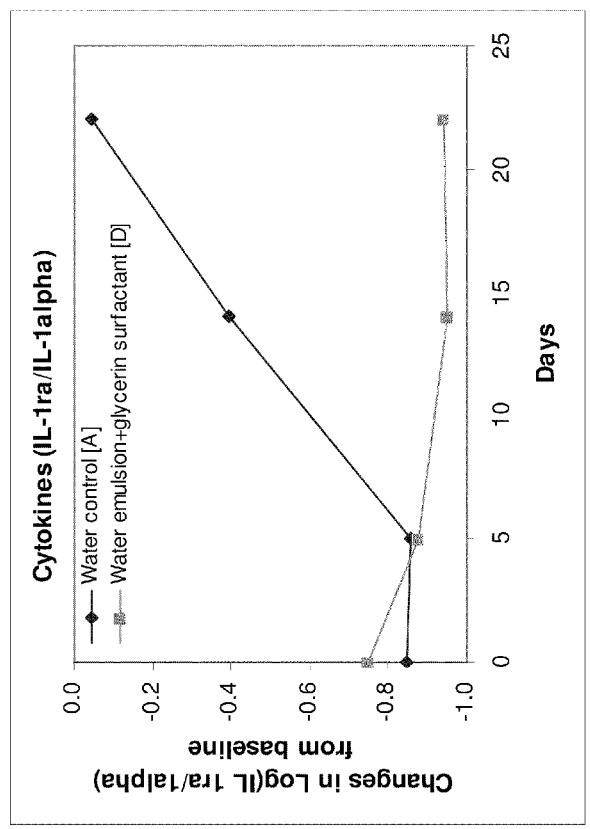
FIG. 4 shows results of cytokine biomarker measurement comparing water and a test composition in a representative clinical study, demonstrating that test compositions can affect measurable and significant changes in skin biology.
Figure 5:
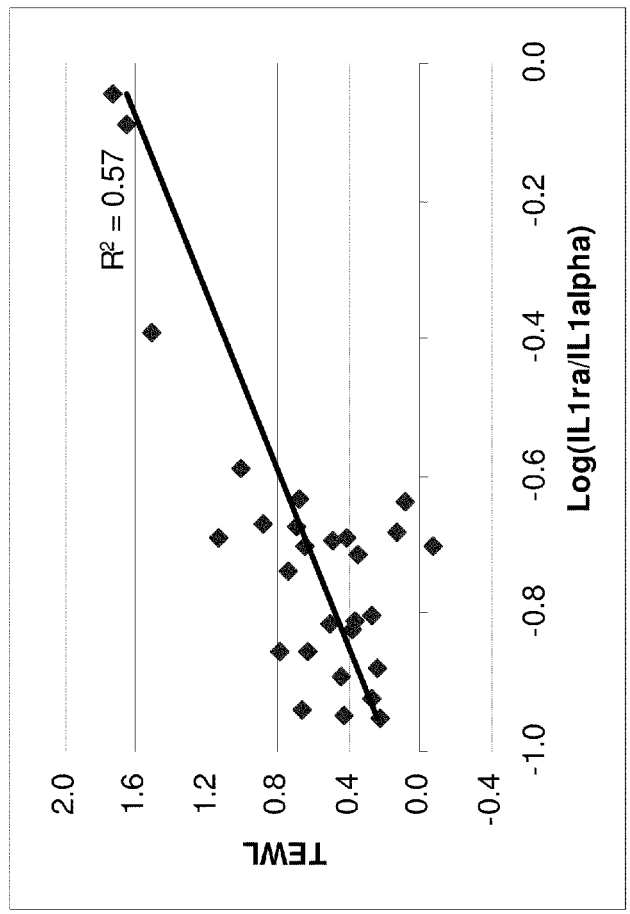
FIG. 5 shows the correlation of objective physical measurement of trans-epidermal water loss with results of cytokine biomarker measurement in a representative clinical study, demonstrating that biomarker measurements correlate well with measurement of skin health.

As more particularly described herein below, the following observations were made regarding the biological responses reflected by the biomarker testing. Referring to FIG. 4 and FIG. 5 and the tables and description in Example 1 hereof, we discovered that inflammatory cytokines (Log IL 1ra/IL 1α) substantially decreased after 2 weeks of treatment using test compositions in a rinse-off context. Not only were the results surprising since dry skin is not a diseased state, but the magnitude of inflammation reduction was equally surprising. The decrease of Log IL 1ra/IL 1α was up to 8 fold as compared to water control. Cytokine reduction trends well with barrier function improvement (TEWL) ($R^2=0.57$).

Figure 6:
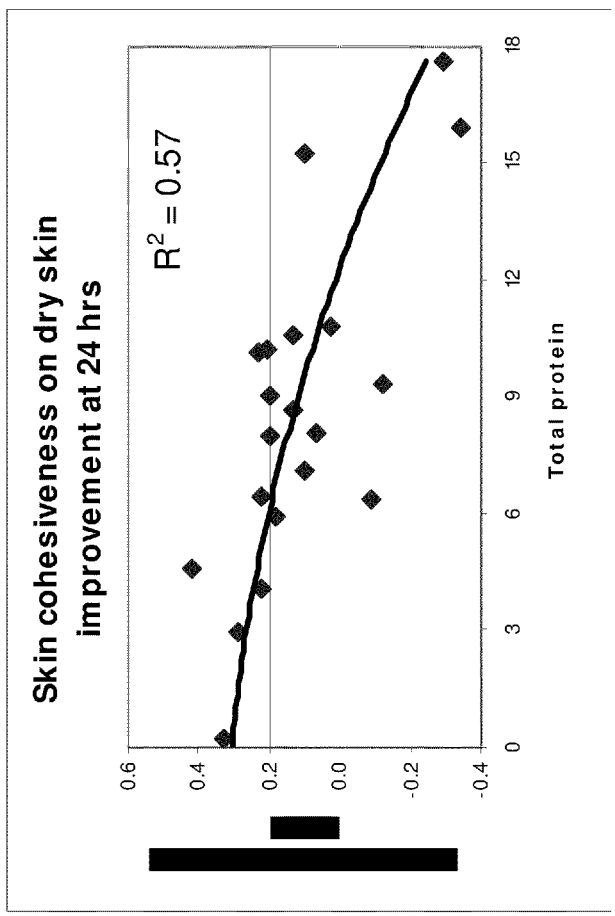
FIG. 6 shows the correlation of objective physical measurement of skin cohesiveness on dryness improvement with results of total protein biomarker measurement in a representative clinical study at 24 hours, demonstrating that biomarker measurements correlate well with measurement of skin health.
Figure 7:
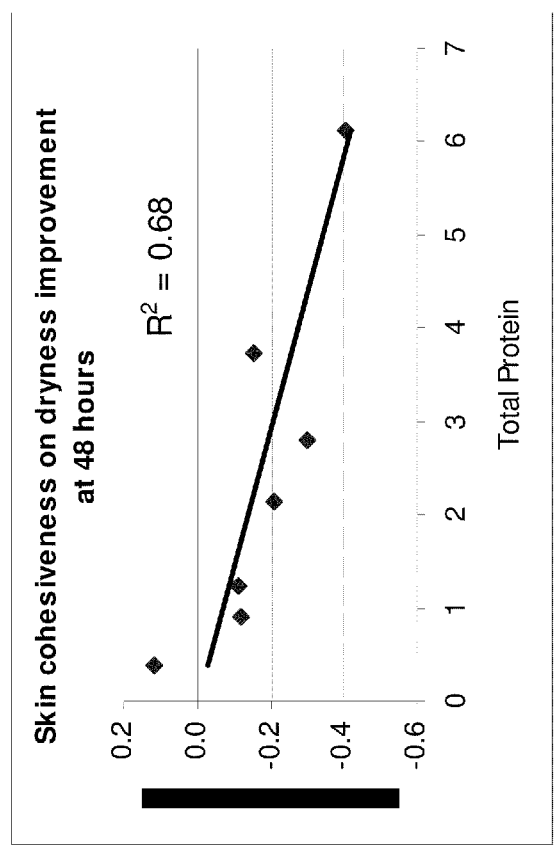
FIG. 7 shows the correlation of objective physical measurement of skin cohesiveness on dryness improvement with results of total protein biomarker measurement in a representative clinical study at 48 hours, demonstrating that biomarker measurements correlate well with measurement of skin health.

Our results also show that total protein appears to be an early showing biomarker. Referring now to FIG. 6 and FIG. 7 and Examples 1 and 2 hereof, in testing of agents in a rinse-off context, most of the test compositions showed meaningful differentiation from water control as soon as after 4 treatments, while the benefit continued throughout the test period. As reported herein below, total protein correlates with dry skin improvement with $R^2=0.57$ and 0.68 at 24 and 48 hour time points.

Referring now to Tables shown in Example 1, also in a rinse-off context, the level of natural moisturizing factors started at a lower level than water control, likely because of surfactant effects. However, it was observed over time that the surfactant effects diminished, and the test agents ultimately surpassed and trended better than the water control in terms of demonstrated increase in the NMF biomarkers.

Figure 8:
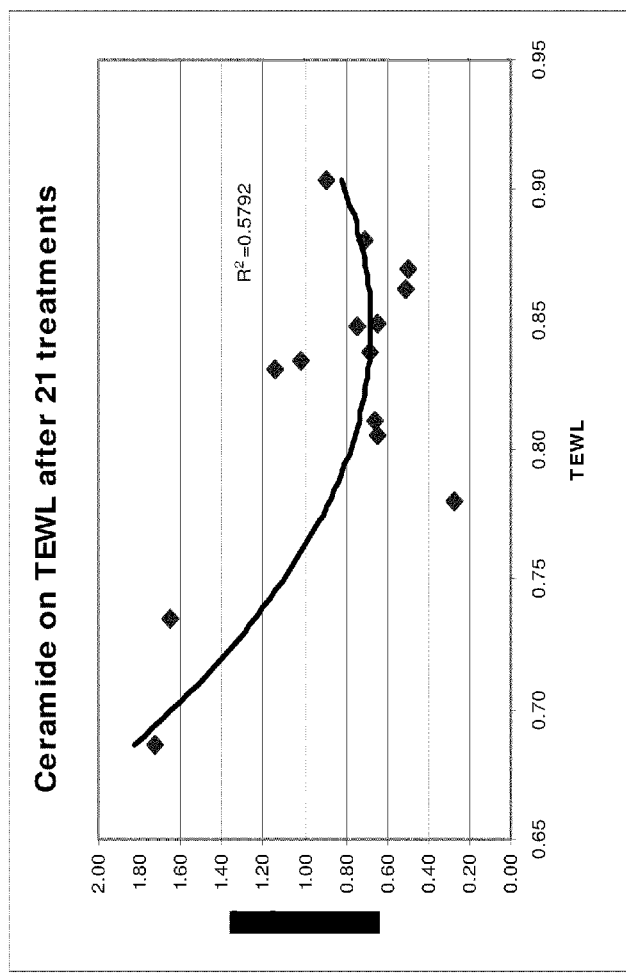
FIG. 8 shows the correlation of objective physical measurement of trans-epidermal water loss improvement with results of lipid (ceramides) biomarker measurement in a representative clinical study, demonstrating that biomarker measurements correlate well with measurement of skin health.

Referring now to FIG. 8, Ceramides of skin lipids showed significant enhancement with most test agents in a rinse-off context, with improvements measured as soon as after 4 treatments compared to water control.

Referring now to FIGS. 18-21, the biomarker panels including total protein, NMF, keratin 1, 10 and 11 and cytokines correlated well with traditional physical measures of TEWL, dryness, corneometer and elasticity, and provided strong predictability ($R^2=0.65-0.74$) of benefit to skin health.

In some embodiments, the methods hereof show that the quality of a subject's skin after a treatment cycle comprising at least one conditioning stage exhibits improvement sufficient to be detected by measurement of one or more biomarkers that include biomarker analytes include inflammatory cytokines, natural moisturizing factors, keratin 1, keratin 10, keratin 11, lipids and total protein.

In some embodiments, effectiveness of treatment is evidenced by detection of variations (or lack thereof) in at least one of biomarker indicators or physical properties of a subject's skin after treatment cycle, as compared to normal healthy control skin. In some embodiments, effectiveness of treatment is evidenced by no measurable variations in at least one biomarker indicator or physical property.

Improvement Indices for Biomarkers

As set forth in Examples 1, 2 and 3 hereof, indices of improvement were determined for each of the biomarkers in the panel described herein.

In some examples, effectiveness of treatment with a test composition is evidenced by an increase in the amount of one or more of keratin 1, keratin 10, and keratin 11, wherein the keratin improvement index is greater than 20. For example, a keratin improvement index of from about 20 to about 1000, and all points subsumed therein, would be evidence of effectiveness of treatment. Accordingly, a keratin improvement index of 20, 40, 60, 80, 100, 120, 140, 160, 180, 200, 220, 240, 260, 280, 300, 320, 340, 360, 380, 400, 420, 440, 460, 480, 500, 520, 540, 560, 580, 600, 620, 640, 660, 680, 700, 720, 740, 760, 780, 800, 820, 840, 860, 880, 900, 920, 940, 960, 980, or 1000 would be evidence of effectiveness of treatment. An effective increase in the amount of one or more of keratin 1, keratin 10, and keratin 11 may be achieved after a suitable period of time after application of the product, for example, after one hour from application, or in another example, after several days of application.

In some embodiments, effectiveness of treatment with a test composition is evidenced by a decrease in the amount of one or more inflammatory cytokines, wherein the cytokine improvement index is greater than 5. For example, a cytokine improvement index of from about 5 to about 2000, and all points subsumed therein, would be evidence of effectiveness of treatment. Accordingly, a cytokine improvement index of 5, 6, 7, 8, 9, 10, 11, 12, 13, 14, 15, 16, 17, 18, 19, 20, 40, 60, 80, 100, 120, 140, 160, 180, 200, 220, 240, 260, 280, 300, 320, 340, 360, 380, 400, 420, 440, 460, 480, 500, 520, 540, 560, 580, 600, 620, 640, 660, 680, 700, 720, 740, 760, 780, 800, 820, 840, 860, 880, 900, 920, 940, 960, 980, 1000, 1100, 1200, 1300, 1400, 1500, 1600, 1700, 1800, 1900 or 2000 would be evidence of effectiveness of treatment. An effective decrease in the amount of one or more inflammatory cytokines may be achieved after a suitable period of time after application of the product, for example, after twenty four hours from application, or in another example, after several days of application.

In some embodiments, effectiveness of treatment with a test composition is evidenced by an increase in the amount of NMFs, wherein the NMF improvement index is from about (−1) to about 25, and all points subsumed therein, would be evidence of effectiveness of treatment. Accordingly, a NMF improvement index of (−1), (−0.9), (−0.8), (−0.7), (−0.6), (−0.5), (−0.4), (−0.3), (−0.2), (−0.1), (−0.09), (−0.08), (−0.07), (−0.06), (−0.05), (−0.04), (−0.03), (−0.02), (−0.01), 0.00, 0.1, 0.2, 0.3, 0.4, 0.5, 0.6, 0.7, 0.8, 0.9, 10. 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0 to 4, 5, 6, 7, 8, 9, 10, 11, 12, 13, 14, 15, 16, 17, 18, 19, 20, 21, 22, 23, 24, or 25 would be evidence of effectiveness of treatment. An effective increase in the amount of NMF may be achieved after a suitable period of time after application of the product, for example, after twenty four hours from application, or in another example, after several days of application.

In some embodiments, effectiveness of treatment with a test composition is evidenced by an increase in the amount of lipids, including ceramides and fatty acids, wherein the ceramides improvement index is greater than 5, and the fatty acids improvement index is greater than 5. For example, a ceramides improvement index of from about 5 to about 500, and all points subsumed therein, would be evidence of effectiveness of treatment. Accordingly, a ceramides improvement index of 5, 6, 7, 8, 9, 10, 20, 20, 40, 50, 60, 70, 80, 90, 100, 110, 120, 130, 140, 150, 160, 170, 180, 190, 200, 300, 400 or 500 would be evidence of effectiveness of treatment. Likewise, a fatty acids improvement index of 5, 6, 7, 8, 9, 10, 20, 20, 40, 50, 60, 70, 80, 90, 100, 110, 120, 130, 140, 150, 160, 170, 180, 190, 200, 300, or 400 would be evidence of effectiveness of treatment. An effective increase in the amount of one or more lipids may be achieved after a suitable period of time after application of the product, for example, after twenty four hours from application, or in another example, after several days of application.

Measurement of Physical Properties Indicative of Skin Health

As set forth in Examples 1, 2 and 3 hereof, indices of improvement were determined for each of the skin health physical measurements described herein.

In some embodiments, physical properties are measured using objective tools and techniques that include: reduction of visual dryness, reduction in trans-epidermal water loss, increased skin hydration, increased elastic extension, increased elastic recovery, and increased firmness, as compared to normal healthy control skin. Also, the quality of a subject's skin after a treatment cycle comprising at least one conditioning stage exhibits improvement sufficient to be detected by measurement of one or more.

In some examples, wherein the effects of biomarkers may be correlated with one or more physical measures, effectiveness of treatment is evidenced by a reduction of visual dryness, wherein the reduction is greater than 0.5 dryness units, as compared to water control. For example, a reduction by from about 0.5 to about 5.0 dryness units, and all points subsumed therein, would be evidence of effectiveness of treatment. Accordingly, a reduction of 0.5, 1.0, 1.5, 2.0, 2.5, 3.0, 3.5, 4.0, 4.5, 5.0, 5.5, 6.0, 6.5, 7.0, 7.5, 8.0, 8.5, 9.0, 9.5, or 10.0 would be evidence of effectiveness of treatment. An effective reduction of visual dryness may be achieved after a suitable period of time after application of the product, for example, after three hours from application.

In some examples, effectiveness of treatment is evidenced by a reduction of trans-epidermal water loss, wherein the reduction is greater than 0.2 TEWL units, as compared to water control. For example, a reduction by from about 0.2 to about 2.0 TEWL units, and all points subsumed therein, would be evidence of effectiveness of treatment. Accordingly, a reduction of 0.2, 0.4, 0.6, 0.8, 1.0, 1.2, 1.4, 1.6, 1.8, or 2.0 would be evidence of effectiveness of treatment. An effective reduction of trans-epidermal water loss may be achieved after a suitable period of time after application of the product, for example, after three hours from application.

In some examples, effectiveness of treatment is evidenced by an increase in skin hydration, wherein the increase is greater than one Corneometer Unit, as compared to water control. For example, an increase of from about one to about 20 Corneometer Units, and all points subsumed therein, would be evidence of effectiveness of treatment. Accordingly, an increase of 1, 2, 3, 4, 5, 6, 7, 8, 9, 10, 11, 12, 13, 14, 15, 16, 17, 18, 19, or 20 would be evidence of effectiveness of treatment. An effective increase in skin hydration may be achieved after a suitable period of time after application of the product, for example, after three hours from application.

In some examples, effectiveness of treatment is evidenced by an increase in elastic extension, wherein the elastic extension improvement index is greater than 5. For example, an elastic extension improvement index of from about 5 to about 50, and all points subsumed therein, would be evidence of effectiveness of treatment. Accordingly, an elastic extension improvement index of 5, 10, 15, 20, 25, 30, 35, 40, 45, or 50 would be evidence of effectiveness of treatment. An effective increase in elastic extension may be achieved after a suitable period of time after application of the product, for example, after one hour from application, or in another example, after several days of application.

In some examples, effectiveness of treatment is evidenced by an increase in elastic recovery, wherein the elastic recovery improvement index is greater than 5. For example, an elastic recovery improvement index of from about 5 to about 50, and all points subsumed therein, would be evidence of effectiveness of treatment. Accordingly, an elastic recovery improvement index of 5, 10, 15, 20, 25, 30, 35, 40, 45, or 50 would be evidence of effectiveness of treatment. An effective increase in elastic recovery may be achieved after a suitable period of time after application of the product, for example, after one hour from application, or in another example, after several days of application.

In some examples, effectiveness of treatment is evidenced by an increase in skin firmness, wherein the skin firmness improvement index is greater than 4. For example, a skin firmness improvement index of from about 4 to about 20, and all points subsumed therein, would be evidence of effectiveness of treatment. Accordingly, a skin firmness improvement index of 4, 8, 12, 16, or 20 would be evidence of effectiveness of treatment. An effective increase in skin firmness may be achieved after a suitable period of time after application of the product, for example, after one hour from application, or in another example, after several days of application.

In some examples, effectiveness of treatment is evidenced by a reduction in total protein, wherein the total protein improvement index is greater than 5. For example, a total protein improvement index of from about 5 to about 50, and all points subsumed therein, would be evidence of effectiveness of treatment. Accordingly, a total protein improvement index of 5, 10, 15, 20, 25, 30, 35, 40, 45, or 50 would be evidence of effectiveness of treatment. An effective reduction in total protein may be achieved after a suitable period of time after application of the product, for example, after twenty four hours from application, or in another example, after several days of application.

Thus, in accordance with the various embodiments described herein, potential product formulations and actives may be tested for their effects on skin health, wherein effectiveness of the treatment is evidenced by improvement or maintenance of at least one biomarker. It will be appreciated that the physical and biomarker indicators of skin quality are not limited to those identified herein and that other biomarkers later discovered or currently known in the art may also be assessed to determine the usefulness of a test agent for maintenance or improvement of skin quality according to the methods hereof.

Formulating for Populations

It will be appreciated that the methods hereof are useful for benefiting users from a variety of populations. Accordingly, also provided are methods for developing personal care compositions and regimens of treatment for members of various populations. The methods involve testing proposed compositions or formulations on a plurality of individual subjects in a target population whereby the formulated personal care composition is optimized based on the measured biomarker responses in the target population.

In some embodiments, the steps further include manufacturing the composition for the target population; and providing the composition in the delivery article. It will be appreciated that the method may be repeated for a different target population.

III. METHODS AND REGIMENS FOR TREATING SKIN

Also provided are methods for improving the quality of skin that are evidenced by measurable improvement in one or more biomarker indicators. According to such methods, in some embodiments, the steps include dispensing from a personal care article a personal care composition that comprises a hydrophobic benefit phase and a lathering phase in a rinse-off formulation, applying the personal care composition to a subject's skin together with water, rinsing the personal care composition from the subject's skin, wherein a portion of the hydrophobic benefit phase is deposited and remains on the subject's skin after rinsing. According to such embodiments, the steps further include repeating the steps of applying and rinsing on at least a once daily basis over a time interval of successive days, the time interval of use sufficient to permit detection of measurable improvement in at least one biomarker. Thus, in some specific examples, the biomarker may be selected from inflammatory cytokines, natural moisturizing factors, keratin 1, keratin 10, keratin 11, lipids and total protein. Optionally, additional characterization may be achieved by measuring one or more physical properties to show improvement in skin condition.

According to the various embodiments, evidence of improvement based on physical properties and biomarkers is determined using general analytic methods known in the art. It will be appreciated, though, that this disclosure is the first known reported instance in which measurable improvement in one or more skin biomarkers has been reported in the context of a rinse-off personal care product. Moreover, it will be appreciated that this is the first known reported instance wherein a regimen involving the use of a rinse-off composition having a varied benefit agent profile as described herein has been employed. Thus, we believe we are the first to report the employment of biomarker and physical property measurements of skin to show measurable improvement in one or more properties after treatment according to the instant disclosure. As more fully described in the examples herein, methods for measuring physical properties and skin biomarkers have been employed to demonstrate the effectiveness of the methods hereof.

The personal care compositions used in accordance with the present disclosure are used in a conventional manner for use on skin, for example, for cleansing and conditioning skin. Typically, the personal care compositions used in accordance with the present disclosure are applied topically to the desired area of the skin in an amount sufficient to provide effective delivery of the actives. The compositions can be applied directly to the skin or indirectly via the use of an applicator pad or brush, cleansing puff, washcloth, sponge or other implement. The compositions are in some instances typically diluted with water prior to, during, or after topical application, and then subsequently the skin is rinsed or wiped off, typically rinsed off of the applied surface using water or a water-insoluble substrate in combination with water.

The present disclosure is therefore in some embodiments directed to methods of cleansing the skin through the above-described application of the compositions as disclosed herein. An effective amount of the composition for cleansing and conditioning the skin is applied to the skin, that in some examples has been wetted with water, and then rinsed off. Such effective amounts generally range from about 1 gm to about 50 gm, and from about 1 gm to about 20 gm.

In general, a typical method for cleansing and conditioning the skin comprises the steps of: a) wetting the skin with water, b) applying an effective amount of the personal care composition to the skin, and c) rinsing the applied areas of skin with water. These steps can be repeated as many times as desired to achieve the desired cleansing and conditioning benefit.

Treatment Methods

The present disclosure is directed in some aspects to methods and regimens for improving or maintaining the quality of skin through use of personal care compositions. In some aspects, the methods are useful for sustaining consumer use of a treatment for skin.

In accordance with various embodiments, the methods comprise delivery of two or more skin active or benefit agents to the skin of a user, particularly lathering and hydrophobic benefit phases, to provide resulting benefits from such delivery, as described herein. The personal care compositions are formulated in various embodiments with sufficient amounts of each of the benefit agents to provide one or both of superior/premium lather performance and stability and superior/premium hydrophobic benefit phase deposition for extended conditioning. Superior lather performance can be demonstrated via the lather volume test method described herein. Superior hydrophobic benefit phase deposition and associated extended skin conditioning can be demonstrated via the various physical tests and biomarker tests described herein below.

Figure 2:
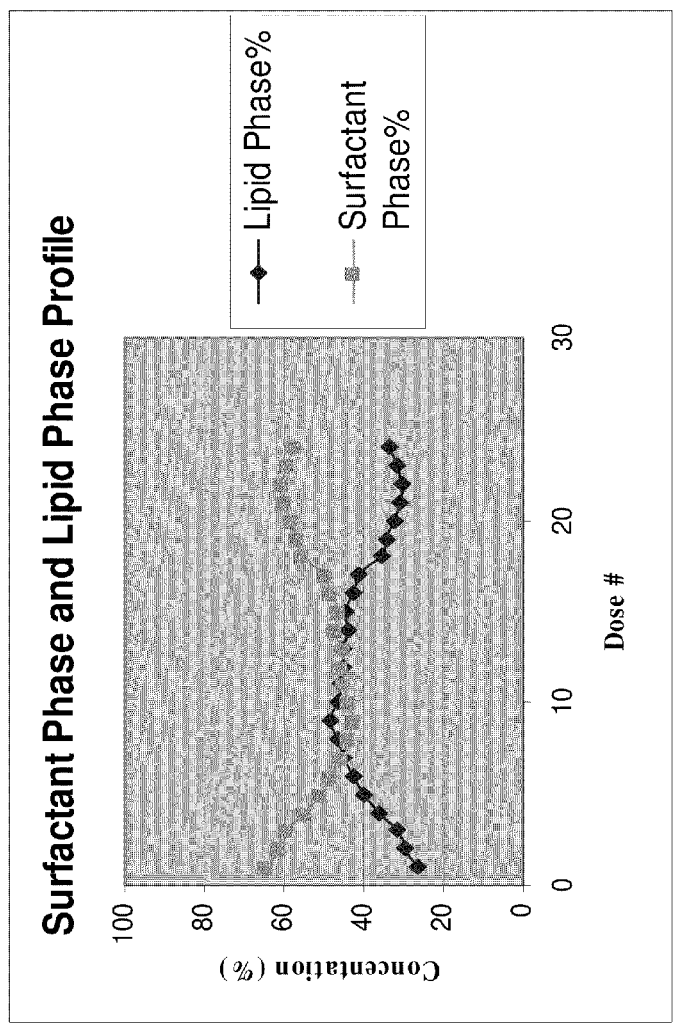
FIG. 2 shows an exemplary profile of lathering phase to hydrophobic benefit phase.
Figure 3:
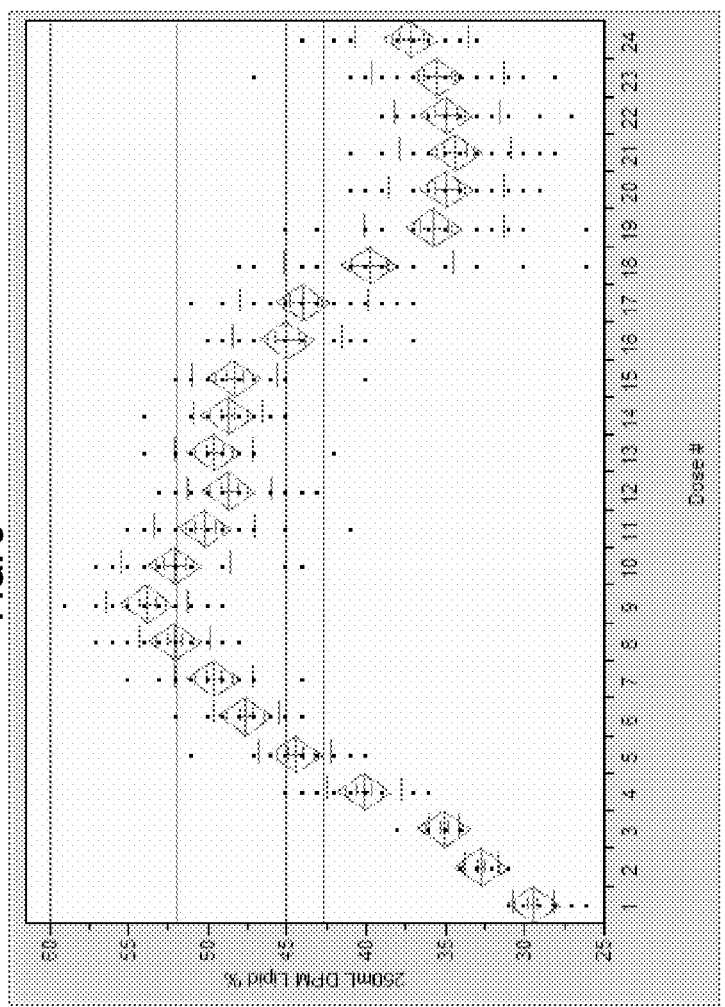
FIG. 3 shows a delivery profile for an exemplary personal care composition comprising lathering phase and hydrophobic benefit phase wherein the ratio of lathering phase to hydrophobic benefit phase varies across a treatment cycle from about 70:30 through about 45:55 to about 80:20, wherein the volume of dispensed composition is 250 ml.

FIG. 2 shows an exemplary profile of lathering phase to hydrophobic benefit phase. As can be seen, one curve describes the dispensing and delivery profile of hydrophobic benefit phase and one curve describes the dispensing and delivery profile of lathering phase over a series of aliquots from a representative article containing 250 ml of product according to the instant disclosure. Of course it will be appreciated that other volumes of product are contemplated, and that the ratio of lathering phase to hydrophobic benefit phase may vary depending on the package features and the fill profile of hydrophobic benefit phase to lathering phase. It will also be appreciated that, as described further herein below that additional benefit agents may be included and as such, any such additional agent may follow the profile of either the hydrophobic benefit phase or the lathering phase or may have a different profile. FIG. 3 shows a dispensing profile for the product exemplified in FIG. 2 indicating the amount of hydrophobic benefit phase by percent delivered in the sequential aliquots as a function of dose.

In some embodiments, the compositions can comprise additional benefit agents, such as fragrances, exfoliates/desquamates, lightening and other optional agents as further described herein. It is contemplated according to the various embodiments that the two or more skin benefit agents are delivered in varying relative quantities, as more fully described herein below. It will be appreciated that additional benefit agents may be delivered together with one or the other benefit agents such that quantities of such additional benefit agents varies synchronously with one of the other benefit agents. It will further be appreciated that each of two, three or more benefit agents may each be delivered in varying relative quantities that are not in synchrony with any of the other benefit agents.

The personal care compositions used in accordance with the embodiments disclosed herein are typically liquid or semi-liquid compositions intended for topical application to the skin, such as the hair or skin. Thus, in some embodiments, the compositions are "rinse-off" formulations, by which is meant the product is applied topically to the hair or skin and then subsequently and immediately (i.e., within minutes) rinsed away with water, or otherwise wiped off using a substrate or other suitable removal means. In accordance with rinse-off composition embodiments, the compositions contain at least one lathering phase and at least one hydrophobic benefit phase, both of which are described in greater detail hereinafter. The personal care compositions are applied topically to the desired area of the skin or hair in an amount sufficient to provide effective delivery of the skin benefit agents to the applied surface, or to otherwise provide effective skin conditioning benefits. The compositions can be applied directly to the skin or indirectly via the use of a cleansing puff, washcloth, sponge or other implement. The compositions are in some embodiments diluted with water prior to, during, or after topical application.

Examples of application and use of some embodiments of personal care compositions are provided herein. Likewise, examples describing the methods for characterizing the premium benefits of the compositions, and for preparing and packaging embodiments of the compositions are provided in the examples sections hereof.

In various embodiments, the methods and regimens comprise use of a personal care composition that comprises at least two skin active or benefit agents, typically a lathering phase (surfactant) and a hydrophobic benefit phase (lipid), wherein the amounts (ratio, by weight) of lathering phase to hydrophobic benefit phase are constant or vary over the course of the regimen. The composition is used over a period of time, alternately referred to as a treatment cycle or treatment time that includes one, two or more sequential stages. It should be understood that the term "stage," as used to describe the methods herein, is intended to be non-limiting with respect to time or sequence of the steps of a treatment cycle. In some embodiments, the treatment cycle includes three stages.

In some embodiments, the treatment cycle comprises at least one stage where the ratio of the lathering phase to the hydrophobic benefit essentially does not vary. It will be appreciated that a treatment cycle can include two, three, four or more stages, and that the ratio of lathering phase to hydrophobic benefit phase may be the same throughout all of the stages, or the ratio may vary between the stages though the ratio remains constant throughout a singe stage.

In alternate embodiments, the ratio of the lathering phase to the hydrophobic benefit phase varies from one stage to the next stage, wherein in some embodiments the ratio of lathering phase to hydrophobic benefit phase is greater in a first stage than in a second stage. In other embodiments, the ratio of lathering phase to hydrophobic benefit phase is lower in a first stage than it is in a second stage. In some embodiments comprising three stages, the ratio of lathering phase to hydrophobic benefit phase is higher in a first stage, declines in a second stage, and increases in a third stage. It will be appreciated that a treatment cycle can include two, three, four or more stages, and that the ratio of lathering phase to hydrophobic benefit phase can vary in a variety of ways between each of the sequential stages, as is described more fully herein below. In accordance with the various embodiments, the methods include the steps of applying the composition to a subject's skin on a daily basis for a period of days.

According to a representative embodiment comprising a treatment cycle of three stages, a first stage is a premium experience stage in which a high lathering phase (surfactant) is used that provides a premium user experience through high lather. Thus, in this first stage, the ratio of lathering phase to hydrophobic benefit phase is high relative to the following stage. According to this representative embodiment, as use progresses into a second stage, a high lipid "plateau" provides conditioning through high hydrophobic benefit phase content. Thus, in this second stage, the ratio of lathering phase to hydrophobic benefit phase is low relative to a first stage. And in a third stage a high lathering phase (surfactant) is used that provides a premium user experience through high lather. Thus, in this third stage, the ratio of lathering phase to hydrophobic benefit phase is high relative to the previous stage. It will be appreciated that the number and sequential order of premium experience and conditioning stages may vary. As mentioned above, in some embodiments a treatment period may comprise only two stages, or it may comprise three or more stages. Irrespective of the number and order of stages, a treatment cycle is characterized in some embodiments as comprising in any order at least one premium experience stage and one conditioning stage.

According to the various embodiments, personal care compositions provide a lathering phase that produces a lather volume. In some embodiments the lather volume of the composition is greater than from about 800 ml to 1500 ml, as tested according to the Lather Volume method described herein. It will thus be appreciated by those in the art that in accordance with the described method, the lather volume provided by a personal care composition may be greater than from about 800, 850, 900, 950, 1000, 1050, 1100, 1150, 1200, 1250, 1300, 1350, 1400, 1450, and 1500 or more ml as well as all points subsumed therein. Of course it will be appreciated that in some embodiments, particularly with respect to embodiments and stages wherein the ratio of lathering phase to hydrophobic benefit phase is low, that the lather volume will be lower or substantially lower than the above stated ranges. In some embodiments the lather volume may be greater than the above ranges, such as from about 1500 to 1750, about 1750 to 1900, about 1900 to 2000 or more ml, as well as all points subsumed therein. It will also be appreciated that other methods described or otherwise known in the art may be used to characterize lather and lather volume and that the description herein is not limiting, such that the lather properties of the compositions used as described herein may be described in other terms.

In accordance with the provided methods, the composition is provided in a delivery article that is adapted for use in accordance with a predetermined time of treatment or a predetermined approximate number of instances of treatment, or both. Thus, in some embodiments, the delivery article is adapted to deliver sufficient composition for one or two or more treatment cycles. In some embodiments, the delivery article is adapted to deliver the composition for each treatment cycle in an approximate number of aliquots or units. In such embodiments, the aliquots may be the same in volume or may vary. In some embodiments the number of aliquots or units to be dispensed per stage or in a delivery article is a predetermined number that defines the approximate number of instances of use, either in days, weeks or months.

In accordance with some embodiments of the methods, the composition is applied on a daily basis. A delivery article as described above may optionally be used for delivery of the composition. It will be appreciated that treatment times and frequency may vary based upon the user, and as such, treatment may be on a less than daily basis, or may be more often. In other embodiments, the treatments may be less frequent, for example weekly or monthly, or in some other interval of time.

As described herein above with respect to the stratum corneum, that is, the outermost layer of the skin, that the cycle of cell turnover in the epidermis from the basal stratum to the stratum corneum is on the order of about a month, or from about 27 to 30 days. In addition, the average sloughing (desquamation) time of cells from the stratum corneum is on the order of about two weeks, or from about 12-14 days. It has been appreciated with respect to the methods hereof, that treatment cycles adapted to the biology of the skin are surprisingly effective in improving and maintaining the normal function and healthy quality of skin, as more fully described herein with respect to the characterization of skin properties. Thus, treatment cycles which span the typical epidermal cell cycle (for keratinocytes) and which include at least one conditioning stage of about a week have been demonstrated to be effective, as described herein.

In some embodiments of the methods hereof the composition is applied through a treatment cycle in a time interval of about thirty days. For example, a first stage of the treatment cycle may be from about 3 to 7 days, a second stage of the treatment cycle may be from about 6 to 14 days, and a third stage of the treatment cycle may be from about 6 to 14 days. In another example, a first stage of the treatment cycle may be from about 2 to 5 days, a second stage of the treatment cycle may be from about 3 to 7 days, and a third stage of the treatment cycle may be from about 14 to 21 days. In accordance with these examples, in some embodiments the first and third stages are premium experience stages, wherein the delivery of lathering phase and associated lather volume is high as compared with the second, conditioning stage, wherein the delivery of hydrophobic benefit phase is high.

It will be appreciated that according to the methods, a treatment cycle may be repeated two or more times. According to various embodiments, repeated treatment cycles may have the same number and order of stages and may be of the same length of time. Of course, in other embodiments, sequential treatment cycles may each have different numbers and orders of stages and may be of varying lengths of time. In accordance with a representative embodiment of a treatment cycle as described above, wherein the cycle is about 30 days or one month, the treatment cycle may be repeated one or more times. Thus, in a series of two treatment cycles, there are six stages ordered as premium experience, conditioning, premium experience, premium experience, conditioning, premium experience. As in the example described above, the number of days of each cycle may be as described, or the number of days may be as described in alternate embodiments described below.

In other embodiments, the composition is applied through a treatment cycle in a time interval of about fifty days. In one example, a first stage of the treatment cycle may be from about 3 to 7 days, a second stage of the treatment cycle may be from about 10 to 28 days, and a third stage of the treatment cycle may be from about 14 to 20 days. In other embodiments, the composition is applied through a treatment cycle in a time interval of about fifty-six days. In one example, a first stage of the treatment cycle may be from about 2 to 7 days, a second stage of the treatment cycle may be from about 3 to 28 days, and a third stage of the treatment cycle may be from about 6 to 21 days.

Optionally, the composition used in accordance with the methods may comprise an additional benefit agent, non-limiting examples of which include vitamins, vitamin derivatives, sunscreens, desquamation actives, anti-wrinkle actives, anti-atrophy actives, anti-oxidants, skin soothing agents, skin healing agents, skin lightening agents, skin tanning agents, anti-acne medicaments, essential oils, sensates, pigments, colorants, pearlescent agents, interference pigments, particles, hydrophobically modified non-platelet particles and combinations thereof. In one example the additional benefit agent is a fragrance. In accordance with this example, some embodiments the fragrance agent is delivered with the lathering phase such that the premium experience stage is further characterized by delivery of fragrance. Of course, in other embodiments, the additional agent, such as a fragrance agent, may be delivered with the hydrophobic benefit phase so as to provide enhanced experience during the conditioning stage. And of course in yet other embodiments, the additional benefit agent, such as a fragrance agent, may be delivered in with both the lathering and the hydrophobic benefit phases. In some embodiments, more than one additional benefit agents, such as two fragrance agents, may be included and the amount or presence of each may vary through the stages. According to the various embodiments comprising additional benefit agent(s), the additional benefit agent(s) may be provided in a fixed amount or concentration, or in amounts that vary across the stages, or that vary with one or the other of the lathering and hydrophobic benefit phases, or that vary separately from each of the other benefit agents. Other benefit agents and materials as described herein and those known in the art may also be used with respect to representative composition embodiments described herein. Likewise, other formulation components, including other and additional lathering/surfactant agents and hydrophobic benefit phases may be selected as described herein. Additional benefit agents may be provided with either or both the lathering phase and the hydrophobic benefit phase. Examples of some specific benefit agents include exfoliating agents, niacinamide, vitamin E (tocopherol or tocotrieneol), collagen.

The following examples further describe and demonstrate embodiments within the scope of the present disclosure. The examples are given solely for the purpose of illustration and are not to be construed as limitations of the present disclosure, as many variations thereof are possible without departing from the spirit and scope hereof.

IV. EXAMPLES

Example 1

CLINICAL STUDY: EVALUATION OF SKIN INDICATOR RESPONSE AND CYTOKINE, NATURAL MOISTURIZING FACTOR, TOTAL PROTEIN AND LIPID BIOMARKERS; CORRELATIONS BETWEEN BIOMARKERS AND MEASURES OF SKIN HEALTH

The clinical study design was a leg controlled application test (LCAT) protocol for body wash, representative methods are described herein below.

Clinical design and biomarker analysis: Human subjects were screened for dry skin score at 2.5 or higher, in accordance with the dryness grading procedure described herein below. A cohort of 30 subjects was selected for each treatment. All subjects were pre-conditioned with Olay® soap bar for 7 days followed by 1 application/day for 3 weeks and 2 day regression. Measurements included dry skin grade, corneometer, TEWL, cutometer, and tape strips to obtain biomarker analytes. The treatment design is shown in TABLE 1. The formulations for each of the compositions A, B, C, D, E, F, and G are provided in TABLES 2, 3, 4, 5, 6, and 7 below.

TABLE 1

CLINICAL DESIGN

| Leg | Lipid Phase |
|---|---|
| A | Water |
| B | Glycerin emulsion (1.5% GMO, 68.5% G2218Pet, 30% glycerin) + surfactant (50:50) |
| C | Water emulsion (1.5% GMO, 68.5% G2218Pet, 30% water) + surfactant (50:50) |
| D | Water emulsion (1.5% GMO, 68.5% G2218Pet, 30% water) + glycerin (30%) surfactant (50:50) |
| G | Sefose lipid (8.0% sefose 1618H, 2.0% sefose1618U, 90.0% G2218Pet) + surfactant (50:50) |

TABLE 2

SURFACTANT

| CTFA NAME | Percent Composition |
|---|---|
| Water | 31.796% |
| Sodium Lauryl Sulfate | 28.550% |
| Sodium Lauroamphoacetate | 15.940% |
| Sodium Trideceth Sulfate | 12.740% |
| Sodium Chloride | 4.750% |
| Fragrance (Pashmina PCC) | 1.820% |
| Trideceth-3 | 2.00% |
| Methylchloroisothiazolinone, Methylisothiazolinone | 0.091% |
| Citric Acid | 0.895% |
| Guar Hydroxypropyltrimonium Chloride | 0.60% |
| Xanthan Gum | 0.220% |
| Sodium Benzoate | 0.200% |
| PEG-90M | 0.150% |
| Disodium EDTA | 0.150% |
| Sodium Hydroxide | 0.098% |

TABLE 3

GLYCERIN (30%) SURFACTANT

| CTFA NAME | Percent Composition |
|---|---|
| Water | 1.796% |
| Glycerine | 30.000% |
| Sodium Lauryl Sulfate | 28.550% |
| Sodium Lauroamphoacetate | 15.940% |
| Sodium Trideceth Sulfate | 12.740% |
| Sodium Chloride | 4.750% |
| Fragrance | 1.820% |
| Trideceth-3 | 2.00% |
| Methylchloroisothiazolinone, Methylisothiazolinone | 0.091% |
| Citric Acid | 0.895% |
| Guar Hydroxypropyltrimonium Chloride | 0.60% |
| Xanthan Gum | 0.220% |
| Sodium Benzoate | 0.200% |
| PEG-90M | 0.150% |
| Disodium EDTA | 0.150% |
| Sodium Hydroxide | 0.098% |

TABLE 4

1.5% GMO, 68.5% G-2218 PETROLATUM, 30%
GLYCERIN LEG B (+SURFACTANT IN TABLE 2)

| CTFA NAME | Percent Composition |
|---|---|
| Glycerol Monooleate (GMO) | 1.5000 |
| Petrolatum-Low Kaydol | 68.5000 |
| Kosher Superol Glycerine | 30.0000 |
| | 100.0000 |

TABLE 5

1.5% GMO, 68.5% G-2218 PETROLATUM, 30%
WATER LEG C (+SURFACTANT IN TABLE 2)

| CTFA NAME | Percent Composition |
|---|---|
| Glycerol Monooleate | 1.5000 |
| Petrolatum-Low Kaydol | 68.5000 |
| Water | 30.0000 |

TABLE 6

1.5% GMO, 68.5% G-2218 PETROLATUM, 30%
WATER LEG D (+SURFACTANT IN TABLE 3)

| CTFA NAME | Percent Composition |
|---|---|
| Glycerol Monooleate | 1.5000 |
| Petrolatum-Low Kaydol | 68.5000 |
| Water | 30.0000 |

TABLE 7

90.0% G-2218 PETROLATUM, 8.0% SEFOSE 1618H,
2.0% SEFOSE LEG G (+SURFACTANT IN TABLE 2)

| CTFA NAME | Percent Composition |
|---|---|
| .alpha.-D-Glucopyranoside, .beta.-D-fractofuranosyl, octadecanoate (Hardened Sefa Soyate) | 8.0000 |
| Fatty acids C-16-18 and C18-unsaturated esters with Sucrose | 2.0000 |
| Petrolatum-Low Kaydol | 90.0000 |
| | 100.0000 |

Biomarker analysis: Quantitative biomarker analysis included total proteins, cytokines, NMFs, and skin lipids. The tape strips collected from the clinical study were extracted with buffer solutions. Biomarkers in the buffer solutions were quantified via multiplex ELISA and LC/MS/MS and the results were subjected to statistical analysis.

Biomarker Results and Discussion

Cytokines: Cytokines are immunomodulating agents. Specific cytokines evaluated included interleukin 1, alpha (IL 1α) and interleukin 1 receptor antagonist (IL 1ra). It is found in the academic literature that the ratio of IL 1ra and IL 1α is a good indicator for skin inflammation and irritation.

It was quite surprising and unexpected to discover that certain of the compositions tested according to the instant methods significantly reduce log(IL 1ra/IL 1α) vs. the water control after only 14 days, as shown in FIG. 4, particularly in view of the fact that according to conventional wisdom at the time of the instant application, dry skin is not at diseased state. As shown, the magnitude of the log(IL 1ra/IL 1α) is increased up to eightfold.

We analyzed data from physical measurement studies and biomarker analysis for correlations between them, and found that inflammatory cytokine reduction correlates well with the improvements in traditional clinical measurement of dryness, TEWL and corneometer, as shown in FIG. 4 and FIG. 5. This disclosure is the first known report of measurable inflammatory benefits from a body wash composition based on measurement of inflammatory cytokines.

Total proteins: This marker measures protein levels, which in accordance with the method of this study, were captured on the tape. More cohesiveness in healthy stratum corneum produces less protein on the tape strip, while high proteins are predicted to be obtained as a result of less cohesiveness in damaged skin. Referring now to TABLE 8B herein below, results are shown for total protein of 6 tape strips for each test product at 24 hours post treatment time point over a treatment period of 3 weeks and 2 day regression (no treatment). Almost all test products show significant or directional improvement vs. water control (A) at all time points. The products start differentiating from water control as soon as after 4 treatments and the effect reaches the highest point at 3 weeks (22 days). All test products are significantly better than water control after 21 treatments (22 day). Applying a correlation analysis as represented in FIG. 6 and FIG. 7, total protein trends consistently with skin dryness improvement at both 24 and 48 hours. That is, dryness improvement increases as total protein decreases. In other words, skin cohesiveness enhancement is achieved with effective dry skin improvement.

Natural moisturizing factors: Natural moisturizing factor is a collection of water-soluble compounds that are predominantly found in the stratum corneum. These compounds compose approximately 20-30% of the dry weight of a corneocyte. NMF components absorb water from the atmosphere and combine it with their own water content allowing the outermost layers of the stratum corneum to stay hydrated despite exposure to the elements. Referring now to TABLE 8C, results are shown for NMF. NMF measurements in this study included amino acids, lactic acid, urea, and pyrrolidone carboxylic acid. Because NMF components are water soluble, they are easily leached from the cells with water contact, which we propose is why NMF in water control (A) decreases through repeated treatment. NMF levels in products before 14 days are lower than water control. We propose this effect may be a result of surfactants more effectively washing NMF out. Interestingly, most test products reach the same level and some show improvement over water control, and in particular, the glycerin-GMO-Pet emulsion (B) shows directional advantage over water control.

Lipids: The intercellular lipids of the human stratum corneum are unique in composition and quite different from the lipids typically found in biological membranes. They are ideally suited to the formation of permeability barrier because of their high melting point and polarity, which lead to the formation of water-resistant lipid bilayers. The major lipids of the human stratum corneum are ceramides, cholesterol and fatty acids, comprising about 50%, 25% and 10% respectively of the total lipid mass. Referring now to TABLES 8D and 8E, results are shown for ceramides. The ceramides measured and detected include NP-C18, NP-C23, NP-C26, NP-C28, NP-C30, AP-C24, AP-C26, AH-C24, AH-C26, NdS-C24, NdS-C26, EOS-C30. The test products show significant increases in all individual ceramides markers compared to water control after 2 weeks of treatment. Referring now to TABLE 8E, significant increases of the products in fatty acids are observed in all markers measured (C16:0, C16:1, C18:0, C18:1, C18:2). The increase of ceramides trends well with TEWL decrease after 3 week treatment, as shown in FIG. 8.

Tables 8A-8H show detailed clinical results summary data, and include:

TABLE 8A

CYTOKINE, Log(IL 1ra/IL 1α)

| Attribute | Evaluation | Sample Size | Treatment | Statistical Grouping (95% confidence) | Adjusted Mean | Standard Error |
|---|---|---|---|---|---|---|
| Log(IL1ra/IL1Alpha) | Day 1, Baseline | 37 | [A] Water | ab | −0.849 | 0.173 |
| | | 36 | [B] Glycerin emulsion + surfactant | a | −0.996 | 0.174 |
| | | 37 | [C] Water Emulsion + surfactant | ab | −0.879 | 0.173 |
| | | 38 | [D] Water Emulsion + glycerin surfactant | b | −0.745 | 0.172 |
| | | 37 | [G] Sefose lipid + surfactant | a | −0.991 | 0.173 |
| Log(IL1ra/IL1Alpha) | 24 Hr Post Wash 13 (14.0) | 36 | [A] Water | c | −0.392 | 0.113 |
| | | 36 | [B] Glycerin emulsion + surfactant | ab | −0.703 | 0.113 |
| | | 37 | [C] Water Emulsion + surfactant | ab | −0.715 | 0.112 |
| | | 38 | [D] Water Emulsion + glycerin surfactant | a | −0.950 | 0.111 |
| | | 37 | [G] Sefose lipid + surfactant | ab | −0.690 | 0.112 |
| Log(IL1ra/IL1Alpha) | 24 Hr Post Wash 21 (22.0) | 37 | [A] Water | c | −0.046 | 0.120 |
| | | 36 | [B] Glycerin emulsion + surfactant | ab | −0.803 | 0.122 |
| | | 37 | [C] Water Emulsion + surfactant | b | −0.674 | 0.120 |
| | | 37 | [D] Water Emulsion + glycerin surfactant | a | −0.939 | 0.121 |
| | | 37 | [G] Sefose lipid + surfactant | ab | −0.737 | 0.121 |

TABLE 8B

TOTAL PROTEIN (SQUAMESCAN 850 UNIT)

| Attribute | Evaluation | Sample Size | Treatment | Statistical Grouping (95% confidence) | Adjusted Mean | Standard Error |
|---|---|---|---|---|---|---|
| Sum of First 6 Tape Strips | Day 1, Baseline | 36 | [A] Water | a | 117.44 | 3.126 |
| | | 36 | [B] Glycerin emulsion + surfactant | a | 115.95 | 3.125 |
| | | 37 | [C] Water Emulsion + surfactant | a | 115.64 | 3.094 |
| | | 37 | [D] Water Emulsion + glycerin surfactant | a | 114.95 | 3.094 |
| | | 37 | [G] Sefose lipid + surfactant | a | 112.30 | 3.094 |
| Sum of First 6 Tape Strips | 24 Hr Post Wash 21 (22.0) | 37 | [A] Water | b | 132.86 | 2.648 |
| | | 36 | [B] Glycerin emulsion + surfactant | a | 124.26 | 2.645 |
| | | 37 | [C] Water Emulsion + surfactant | a | 121.13 | 2.618 |
| | | 37 | [D] Water Emulsion + glycerin surfactant | a | 123.92 | 2.646 |
| | | 37 | [G] Sefose lipid + surfactant | a | 122.36 | 2.622 |

TABLE 8C

NATURAL MOISTURIZING FACTORS (NMF), Log(Sum NMF/soluble protein)

| Attribute | Evaluation | Sample Size | Treatment | Statistical Grouping (95% confidence) | Adjusted Mean | Standard Error |
|---|---|---|---|---|---|---|
| Log(Sum NMF/soluble protein) | Day 1, Baseline | 36 | [A] Water | a | 3.745 | 0.006 |
|  |  | 36 | [B] Glycerin emulsion + surfactant | a | 3.745 | 0.006 |
| Log(Sum NMF/soluble protein) | 24 Hr Post Wash 13 (14.0) | 36 | [A] Water | a | 3.729 | 0.007 |
|  |  | 36 | [B] Glycerin emulsion + surfactant | a | 3.715 | 0.007 |
| Log(Sum NMF/soluble protein) | 48 Hr Post Wash 21 (23.0) | 37 | [A] Water | ab | 3.735 | 0.005 |
|  |  | 35 | [B] Glycerin emulsion + surfactant | b | 3.746 | 0.005 |

TABLE 8D

CERAMIDES, Log(SumCeramide/soluble protein)

| Attribute | Evaluation | Sample Size | Treatment | Statistical Grouping (95% confidence) | Adjusted Mean | Standard Error |
|---|---|---|---|---|---|---|
| Log(SumCeramide/soluble protein) | Day 1, Baseline | 36 | [A] Water | a | 0.841 | 0.048 |
|  |  | 36 | [B] Glycerin emulsion + surfactant | a | 0.870 | 0.048 |
|  |  | 37 | [C] Water Emulsion + surfactant | a | 0.833 | 0.047 |
|  |  | 37 | [D] Water Emulsion + glycerin surfactant | a | 0.807 | 0.047 |
|  |  | 37 | [G] Sefose lipid + surfactant | a | 0.831 | 0.047 |
| Log(SumCeramide/soluble protein) | 24 Hr Post Wash 13 (14.0) | 36 | [A] Water | ab | 0.846 | 0.046 |
|  |  | 36 | [B] Glycerin emulsion + surfactant | ab | 0.863 | 0.045 |
|  |  | 36 | [C] Water Emulsion + surfactant | abc | 0.880 | 0.045 |
|  |  | 38 | [D] Water Emulsion + glycerin surfactant | bc | 0.958 | 0.045 |
|  |  | 37 | [G] Sefose lipid + surfactant | c | 0.991 | 0.045 |
| Log(SumCeramide/soluble protein) | 24 Hr Post Wash 21 (22.0) | 37 | [A] Water | a | 0.686 | 0.046 |
|  |  | 36 | [B] Glycerin emulsion + surfactant | ab | 0.780 | 0.046 |
|  |  | 37 | [C] Water Emulsion + surfactant | b | 0.880 | 0.046 |
|  |  | 37 | [D] Water Emulsion + glycerin surfactant | b | 0.811 | 0.046 |
|  |  | 37 | [G] Sefose lipid + surfactant | b | 0.847 | 0.046 |

TABLE 8E

FATTY ACIDS, Log(SumFatty acids/soluble protein)

| Attribute | Evaluation | Sample Size | Treatment | Statistical Grouping (95% confidence) | Adjusted Mean | Standard Error |
|---|---|---|---|---|---|---|
| Log(SumFatty acids/soluble protein) | Day 1, Baseline | 36 | [A] Water | a | 2.361 | 0.067 |
|  |  | 36 | [B] Glycerin emulsion + surfactant | b | 2.496 | 0.067 |
|  |  | 37 | [C] Water Emulsion + surfactant | ab | 2.448 | 0.066 |
|  |  | 37 | [D] Water Emulsion + glycerin surfactant | ab | 2.460 | 0.066 |
|  |  | 37 | [G] Sefose lipid + surfactant | ab | 2.438 | 0.066 |
| Log(SumFatty acids/soluble protein) | 24 Hr Post Wash 21 (22.0) | 37 | [A] Water | a | 2.341 | 0.056 |
|  |  | 36 | [B] Glycerin emulsion + surfactant | b | 2.494 | 0.056 |
|  |  | 37 | [C] Water Emulsion + surfactant | b | 2.552 | 0.055 |
|  |  | 37 | [D] Water Emulsion + glycerin surfactant | b | 2.534 | 0.056 |
|  |  | 37 | [G] Sefose lipid + surfactant | b | 2.514 | 0.055 |

TABLE 8F

EXPERT DRYNESS GRADES

| Attribute | Evaluation | Sample Size | Treatment | Statistical Grouping (95% confidence) | Adjusted Mean | Standard Error |
|---|---|---|---|---|---|---|
| Expert dryness grade | Day 1, Baseline | 37 | [A] Water | a | 2.992 | 0.049 |
| | | 36 | [B] Glycerin emulsion + surfactant | a | 3.045 | 0.050 |
| | | 38 | [C] Water Emulsion + surfactant | a | 3.021 | 0.049 |
| | | 37 | [D] Water Emulsion + glycerin surfactant | a | 3.064 | 0.049 |
| | | 37 | [G] Sefose lipid + surfactant | a | 3.011 | 0.049 |
| Expert dryness grade | 24 Hr Post Wash 13 (14.0) | 26 | [A] Water | c | 3.369 | 0.116 |
| | | 30 | [B] Glycerin emulsion + surfactant | ab | 2.997 | 0.110 |
| | | 29 | [C] Water Emulsion + surfactant | a | 2.793 | 0.112 |
| | | 30 | [D] Water Emulsion + glycerin surfactant | a | 2.823 | 0.110 |
| | | 27 | [G] Sefose lipid + surfactant | a | 2.827 | 0.115 |
| Expert dryness grade | 24 Hr Post Wash 21 (22.0) | 37 | [A] Water | b | 3.329 | 0.095 |
| | | 36 | [B] Glycerin emulsion + surfactant | a | 2.840 | 0.096 |
| | | 37 | [C] Water Emulsion + surfactant | a | 2.853 | 0.095 |
| | | 37 | [D] Water Emulsion + glycerin surfactant | a | 2.909 | 0.095 |
| | | 37 | [G] Sefose lipid + surfactant | a | 2.941 | 0.095 |

TABLE 8G

CORNEOMETER RESULTS

| Attribute | Evaluation | Sample Size | Treatment | Statistical Grouping (95% confidence) | Adjusted Mean | Standard Error |
|---|---|---|---|---|---|---|
| Corneometer | Day 1, Baseline | 37 | [A] Water | a | 18.806 | 0.691 |
| | | 36 | [B] Glycerin emulsion + surfactant | a | 18.981 | 0.699 |
| | | 37 | [C] Water Emulsion + surfactant | a | 18.680 | 0.691 |
| | | 38 | [D] Water Emulsion + glycerin surfactant | a | 19.136 | 0.684 |
| | | 37 | [G] Sefose lipid + surfactant | a | 18.613 | 0.691 |
| Corneometer | 24 Hr Post Wash 13 (14.0) | 26 | [A] Water | a | 18.384 | 0.695 |
| | | 30 | [B] Glycerin emulsion + surfactant | b | 20.598 | 0.655 |
| | | 29 | [C] Water Emulsion + surfactant | b | 21.995 | 0.665 |
| | | 30 | [D] Water Emulsion + glycerin surfactant | b | 21.204 | 0.655 |
| | | 27 | [G] Sefose lipid + surfactant | b | 21.223 | 0.687 |
| Corneometer | 24 Hr Post Wash 21 (22.0) | 37 | [A] Water | a | 17.635 | 0.660 |
| | | 36 | [B] Glycerin emulsion + surfactant | bc | 21.973 | 0.667 |
| | | 37 | [C] Water Emulsion + surfactant | c | 22.499 | 0.661 |
| | | 37 | [D] Water Emulsion + glycerin surfactant | bc | 21.588 | 0.660 |
| | | 37 | [G] Sefose lipid + surfactant | bc | 21.492 | 0.661 |

TABLE 8H

TEWL

| Attribute | Evaluation | Sample Size | Treatment | Statistical Grouping (95% confidence) | Adjusted Mean | Standard Error |
|---|---|---|---|---|---|---|
| TEWL readings (Avg. of 2 probes) | Day 1, Baseline | 36 | [A] Water | a | 5.547 | 0.210 |
| | | 36 | [B] Glycerin emulsion + surfactant | a | 5.489 | 0.210 |
| | | 37 | [C] Water Emulsion + surfactant | a | 5.366 | 0.208 |
| | | 38 | [D] Water Emulsion + glycerin surfactant | a | 5.443 | 0.206 |
| | | 37 | [G] Sefose lipid + surfactant | a | 5.450 | 0.208 |

TABLE 8H-continued

TEWL

| Attribute | Evaluation | Sample Size | Treatment | Statistical Grouping (95% confidence) | Adjusted Mean | Standard Error |
|---|---|---|---|---|---|---|
| TEWL readings (Avg. of 2 probes) | 24 Hr Post Wash 13 (14.0) | 26 | [A] Water | b | 6.905 | 0.270 |
| | | 30 | [B] Glycerin emulsion + surfactant | a | 5.314 | 0.255 |
| | | 29 | [C] Water Emulsion + surfactant | a | 5.747 | 0.259 |
| | | 30 | [D] Water Emulsion + glycerin surfactant | a | 5.609 | 0.255 |
| | | 27 | [G] Sefose lipid + surfactant | a | 5.807 | 0.266 |
| TEWL readings (Avg. of 2 probes) | 24 Hr Post Wash 21 (22.0) | 37 | [A] Water | d | 7.200 | 0.181 |
| | | 36 | [B] Glycerin emulsion + surfactant | a | 5.749 | 0.181 |
| | | 37 | [C] Water Emulsion + surfactant | b | 6.176 | 0.179 |
| | | 37 | [D] Water Emulsion + glycerin surfactant | b | 6.134 | 0.179 |
| | | 37 | [G] Sefose lipid + surfactant | b | 6.218 | 0.179 |

Example 2: Clinical Study: Evaluation of Skin Indicator Response and Keratin and Total Protein Biomarkers; Correlations Between Biomarkers and Measures of Skin Health A study was undertaken to evaluate the response of a variety of skin indicators using an array of different personal care compositions and water. The clinical study design was a leg controlled application test (LCAT) protocol for body wash used to evaluate the beneficial effects of personal care products on dry leg skin. Leg wash studies are designed to approximate consumer-relevant exposure levels, e.g. washing frequency. The technique used in this study is a modification of a published procedure (Ertel, et al, 1999).

The study included a product having a variable lipid profile, wherein the ratio of surfactant to lipid (lathering phase to hydrophobic benefit phase) varied continuously between three stages according to the instant disclosure. The study also included a commercially available product having a constant lipid profile. As further described herein below, the compositions used in the study included Inventive Example B and Comparative Example C, as shown in Table 9.

TABLE 9

EXAMPLES OF CONTINUOUS AND VARIABLE LIPID COMPOSITIONS

| | Code B -- Continuous Lipid (55% surfactant to 45% lipid) | Code C -- Variable Lipid (shown in FIG. 9) |
|---|---|---|
| SURFACTANT PHASE | | |
| Sodium Lauroamphoacetate [1] | 4.9 | 4.9 |
| Sodium Trideceth Sulfate [2] | 8.4 | 8.4 |
| Sodium Lauryl Sulfate | 8.4 | 8.4 |
| Trideceth-3 [3] | 2.0 | 2.0 |
| Sodium Chloride | 4.75 | 4.75 |
| Guar hydroxypropyltrimonium chloride [4] | 0.6 | 0.6 |
| Polyethyleneoxide [5] | 0.15 | 0.15 |
| Xanthan gum [6] | 0.2 | 0.2 |
| Hollow microspheres [7] | 0.3 | 0.3 |
| Methyl chloro isothiazolinone and methyl isothiazolinone [8] | 0.0005 | 0.0005 |
| EDTA [9] | 0.15 | 0.15 |
| Sodium Benzoate | 0.2 | 0.2 |

TABLE 9-continued

EXAMPLES OF CONTINUOUS AND VARIABLE LIPID COMPOSITIONS

| | Code B -- Continuous Lipid (55% surfactant to 45% lipid) | Code C -- Variable Lipid (shown in FIG. 9) |
|---|---|---|
| Citric Acid, titrate | pH = 5.7 ± 0.2 | pH = 5.7 ± 0.2 |
| Perfume | 1.3 | 1.3 |
| Water | Q.S. | Q.S. |
| BENEFIT PHASE | | |
| Petrolatum [10] | 70 | 70 |
| Mineral Oil [11] | 30 | 30 |

[1] Available from Cognis Chemical Corp.
[2] sulfanated to >95% sulfate from ICONOL ® TDA-3 available from BASF Corp.,
[3] ICONOL ® TDA-3 available from BASF Corp.,
[4] N-HANCE ® 3196 Polymer from Aqualon of Wilmington, DE,
[5] POLYOX ™ WSR-301 available from DOW ® Chemical Corp.,
[6] KELTRO ™ 1000 available from CP Kelco,
[7] EXPANCEL ® microspheres available from 091 WE40 d24, Akzo Nobel,
[8] KATHON ® CG available for Rohm & Haas,
[9] DISSOLVINE ® NA 2x available from Akzo Nobel,
[10] G2218 petrolatum from Sonneborn,
[11] HYDROBRITE ® 1000 White Mineral Oil available from Sonneborn.

Figure 9:
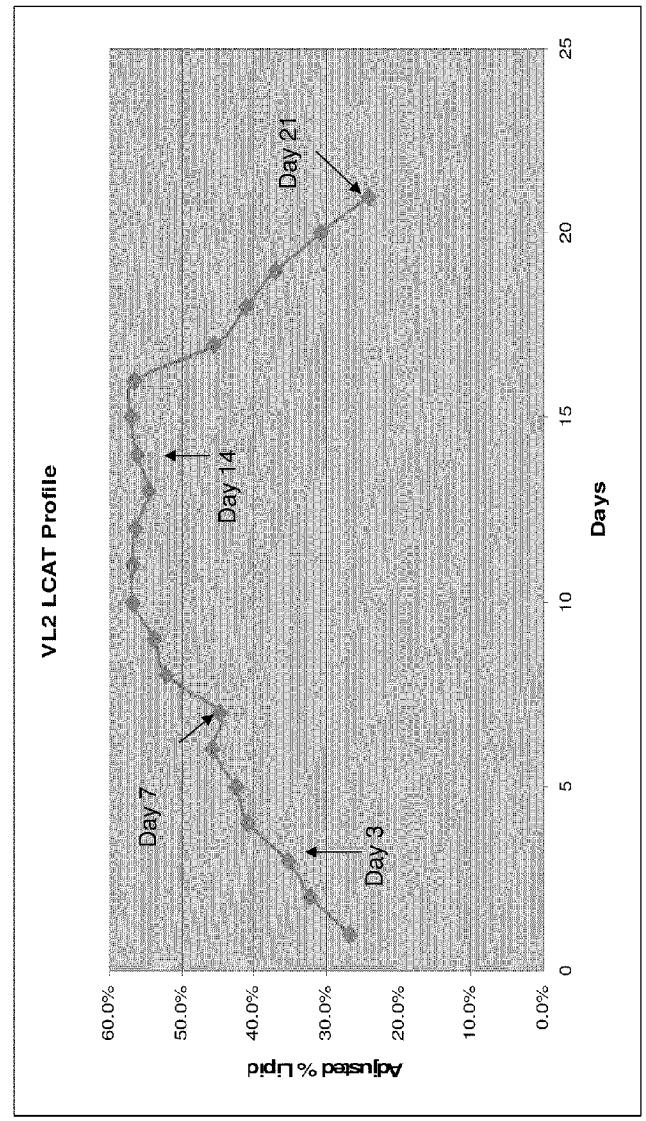
FIG. 9 shows the lipid delivery profile according to an embodiment as described herein wherein the ratio of lathering phase to hydrophobic benefit phase varies across a treatment cycle from about 70:30 through about 45:55 to about 80:20.

FIG. 9 shows a representative dispensing profile for the lipid (hydrophobic benefit phase) in the variable lipid product of the present disclosure. The profile indicates with arrows the treatment days at which certain measurements as described herein were made. Thus, the treatment days are shown with reference to the initiation of treatment after the preconditioning interval; day 1 as shown on FIG. 9 corresponds to study day 8, and so on.

The study was 29 days in duration, with a 7 day interval of preconditioning, 21 days of treatment and 1 regression day. Skin was analyzed at various points from the beginning through the end of the study period. The objective of the study was to characterize the dry skin improvement profile of several body wash prototypes and to generate samples to assess treatment's effects on stratum corneum physical and biomarker indicators. After the 7-day preconditioning stage, subjects returned to the test facility to have the skin on their lower legs evaluated by an expert grader. Only subjects which exhibited sufficient dryness on all of the treatment sites qualified to continue into the treatment stage. Technicians treated each qualified subject's lower legs in a controlled manner with the assigned treatments once daily for 21 days. Subjects' legs were visually evaluated for dryness and redness at several pre and post-treatment times as outlined in the following study schedule. Non-invasive instrumental measurements of stratum corneum hydration (Corneometer 825), barrier function (Dermalab TEWL (trans epidermal water loss)), and viscoelasticity (Cutometer) were made on the treatment sites following visual evaluations.

Treatment Stage Procedure: Before initial grading on Study Day 8, test facility personnel marked off the leg application areas [two 70 $cm^2$-areas (7 cm across×10 cm down)] on the outer aspect of the subjects' lower legs using a template and laboratory marking pen (corner brackets are sufficient to delineate each area). Trained clinical assistants treated each subject's legs according to the procedure outlined in the Treatment Procedure. In general, the following should be noted: The procedure was conducted once each day for 21 consecutive days. The body wash products were applied using puffs (personal cleaning implements). The puff treatment procedure for all puffs was conducted daily after all product treatments were completed on each subject (except on the final day of treatment).

Evaluations: At each evaluation, subjects acclimated for a minimum of 30 minutes in a room with the environment maintained at 70° F.±2 and 30-45% relative humidity prior to visual grading and non-invasive instrumental measurements being made on their legs.

Figure 10:
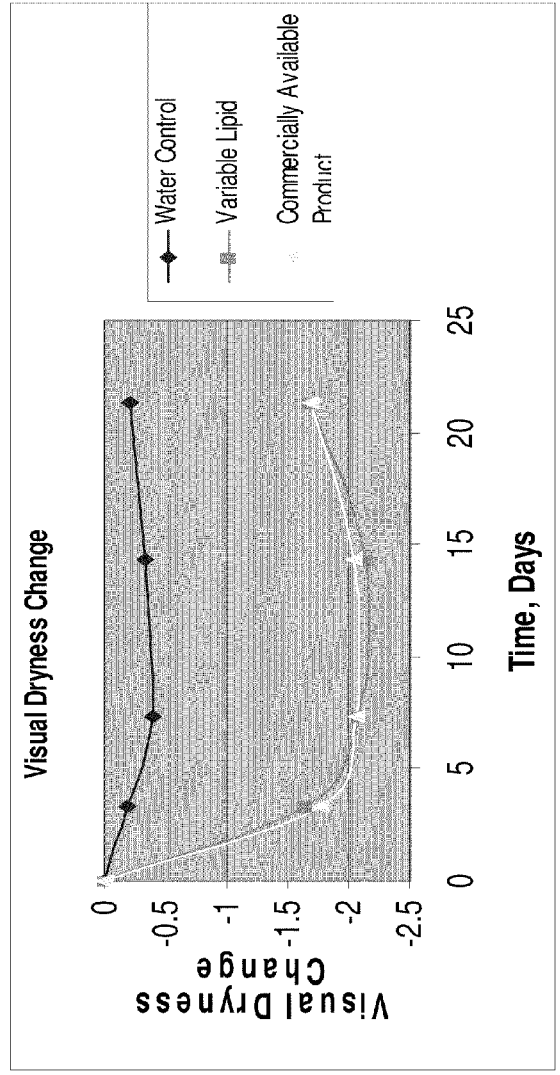
FIG. 10 shows the relative change in visual dryness using water, a personal care composition having a lathering phase to hydrophobic benefit phase ratio of 55:45 and a personal care composition having the lipid delivery profile as shown in FIG. 9.

Visual Grading: Each subject's lower legs were visually evaluated by a qualified grader for dryness and redness at baseline (Study Day 8, prior to the first treatment) as a prerequisite for qualification into the treatment stage. Measurements were made thereafter on study days 10, 12, 21, 28 and 29, at approximately 3 hours post treatment. Referring to FIG. 10, comparative results according to the study are shown.

Figure 11:
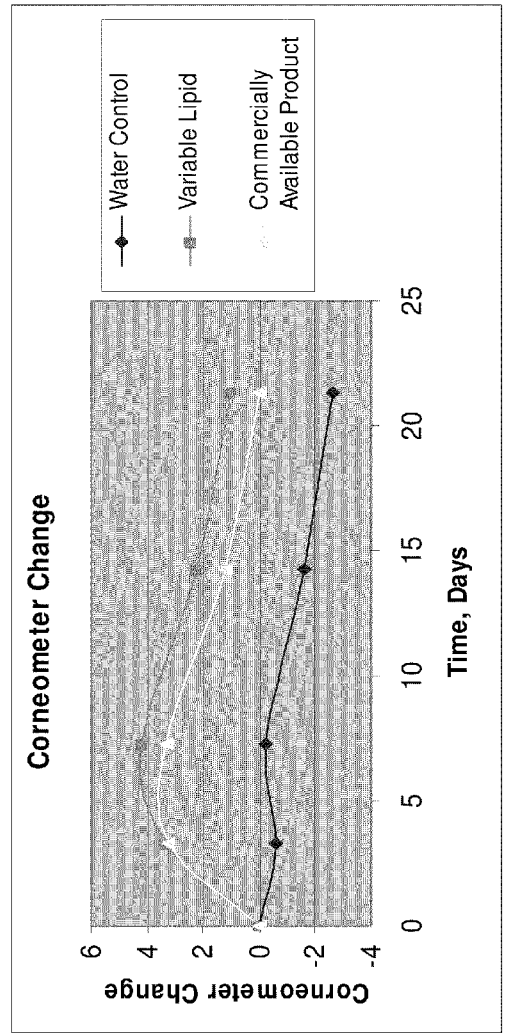
FIG. 11 shows the relative change in skin condition measured with a corneometer using water, a personal care composition having a lathering phase to hydrophobic benefit phase ratio of 55:45 and a personal care composition having the lipid delivery profile as shown in FIG. 9.

Corneometer Skin Capacitance: Non-invasive skin capacitance measurements were taken in duplicate on each site of the subjects' legs after every visual grading during the study using a Corneometer CM825 instrument. Data was recorded electronically using the Sponsor's direct data entry and data capture programs. The same instrument and operator were used throughout the study. Referring to FIG. 11, comparative results according to the study are shown.

Figure 12:
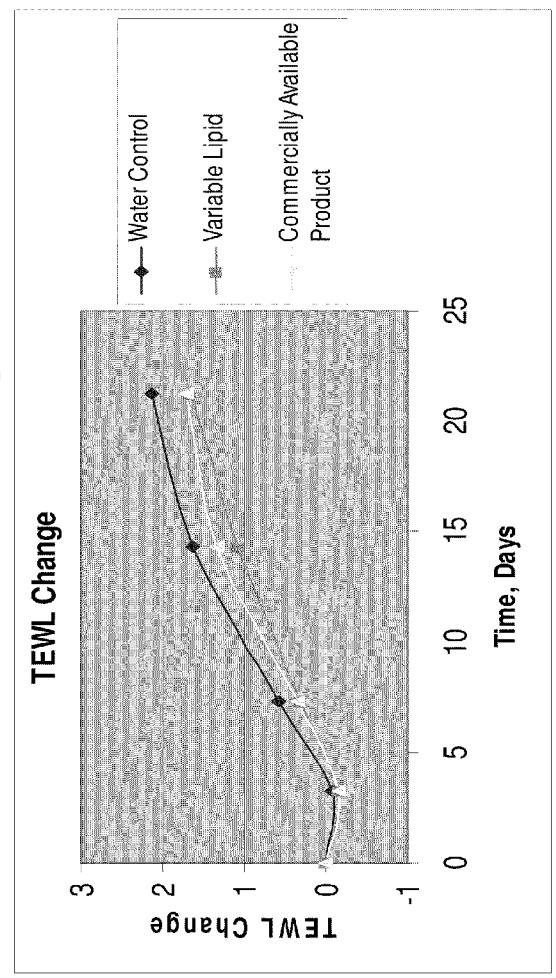
FIG. 12 shows the relative change in skin trans epidermal water loss using water, a personal care composition having a lathering phase to hydrophobic benefit phase ratio of 55:45 and a personal care composition having the lipid delivery profile as shown in FIG. 9.

Trans-epidermal water loss: TEWL was measured with the DermaLab® Evaporimeter equipped with dual probes. Each measurement consists of readings collected for 60 seconds with the mean of the last 20 seconds recorded from both probes (Channel A and Channel B). One measurement was taken at each treatment site and recorded on DCF 2 (DermaLab TEWL Measurements Log) on each evaluation day for both probes as Channel A and Channel B, respectively. The same instrument and operator were used throughout the study. These measurements were made according to procedures outlined in accordance with published guidelines. Measurements were taken 8 times during the course of the study on study days 10, 12, 21, 28 and 29, at approximately 3 hours post treatment. Referring to FIG. 12, comparative results according to the study are shown.

Figure 13:
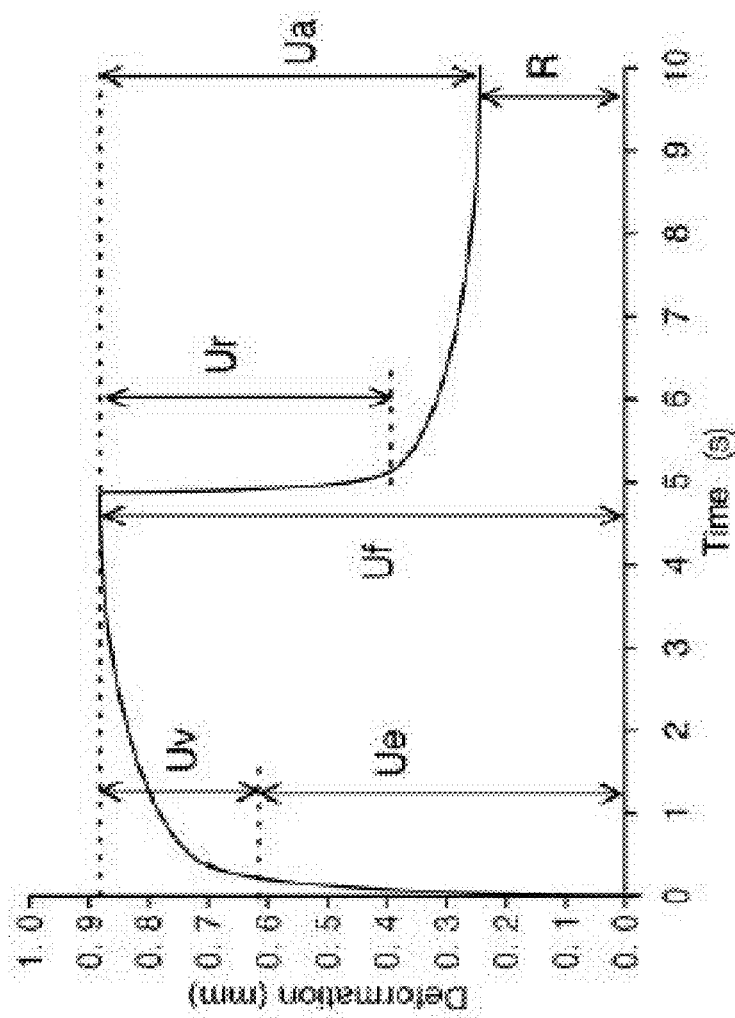
FIG. 13 shows the change in skin deformation over time.
Figure 14:
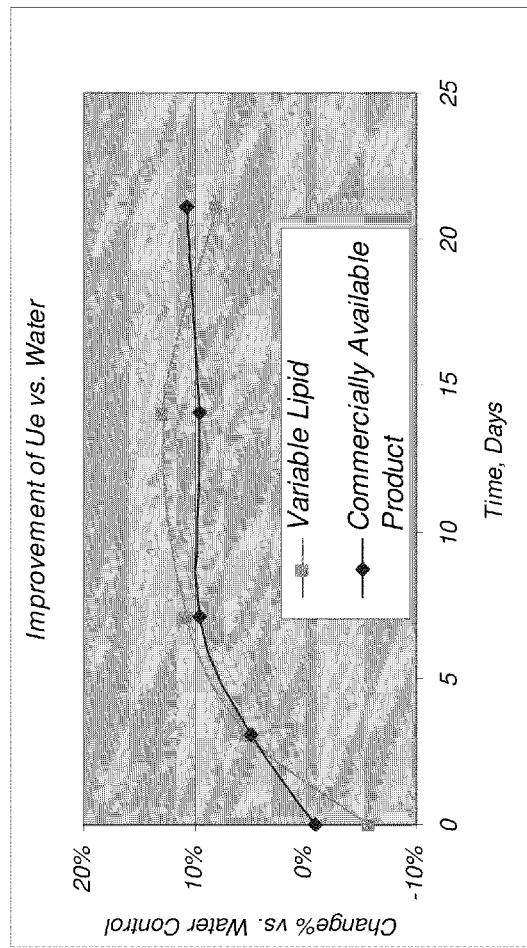
FIG. 14 shows the relative change in Ue using water, a personal care composition having a lathering phase to hydrophobic benefit phase ratio of 55:45 and a embodiment of personal care composition having the lipid delivery profile as shown in FIG. 9.
Figure 15:
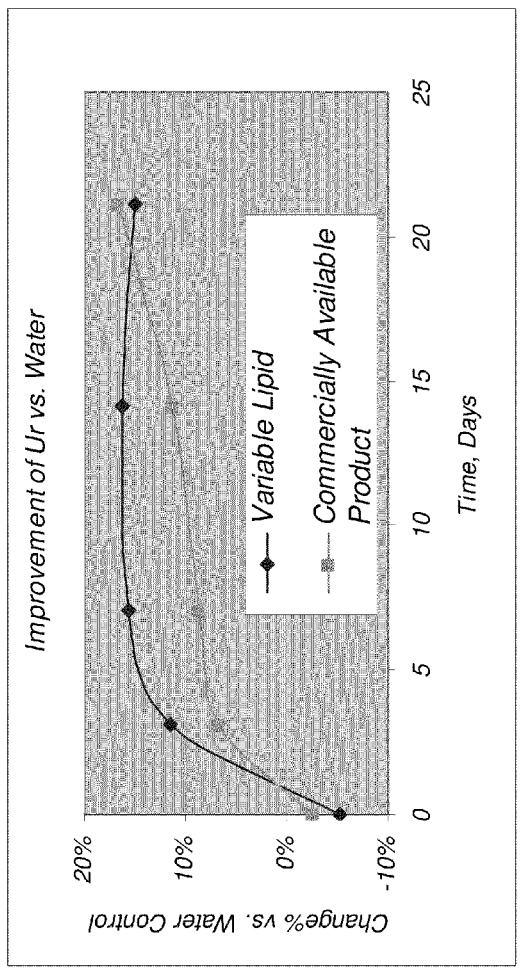
FIG. 15 shows the relative change in Ur using water, a personal care composition having a lathering phase to hydrophobic benefit phase ratio of 55:45 and a personal care composition having the lipid delivery profile as shown in FIG. 9.

Cutometer Measurements of Elasticity: Reapplication of methods typically used for facial skin in a leave-on context was used with a cutometer on legs in a rinse-off personal care composition context. Non-invasive skin viscoelasticity measurements were taken with a Cutometer SEM 575 equipped with an 8 mm probe. Data was recorded electronically using the data capture program accompanying the instrument. Two Cutometer instruments were used due to the number of subjects enrolled in the study. Subjects were assigned to the same instrument throughout the study on the basis of there subject number. The same instruments and operators were used throughout the study. These measurements were made according to the procedures outlined in the Sponsor's instrument SOPs or published guidelines. Measurements were taken 5 times during the course of the study on study days 10, 12, 21, 28 and 29, at approximately 3 hours post treatment. Referring to FIG. 13, FIG. 14 and FIG. 15, comparative results according to the study are shown.

Tape Stripping: Tape stripping was performed throughout the study for dry skin sampling. D-Squames was always collected following all other evaluations scheduled to take place at the same time point. Clinical assistants wore disposable gloves while collecting D-Squames. At each collection time point a series of 6 D-Squames were used to sample the same spot within the treatment area. The technician used forceps to place a D-Squames sampling disc toward the edges of each site (away from the region being evaluated by other instrumentation) and applied pressure using the D-Squames disc applicator (push the D-Squames applicator down and then release). The technician removed the sampling disc with forceps and placed the disc into a pre-labeled 12 well culture plate. Each subject had two 12 well culture plates for sampling disc collection; one for each leg. Wells 1-6 of each plate were for the site nearest the knee, while wells 7-12 were used for the site nearest the ankle. D-Squames sample plates were placed in shipping boxes with labels corresponding to the subjects' samples enclosed and placed in a cooler with dry ice. D-Squames was collected 4 times at the following time points, on study days 8, 12, 21, and 29, at approximately 3 hours post treatment. References: Ertel, K. D., Neumann, P. B., Hartwig, P. M., Rains, G. Y., and Keswick, B. H., Leg Wash protocol to assess the skin moisturization potential of personal cleansing products. *Int. J. Cosmet. Sci.* 21: 383-397 (1999); Fitzpatrick, T. B., The validity and practicality of sun-reactive skin types I through VI. *Arch. Dermatology*, 124: 869-871 (1988).

Soluble Protein and keratin Analyses: Samples were collected for analysis using D-Squame Tape Strips. D-Squame tapes were applied on the leg with constant pressure/time, and removed to collect samples of the stratum corneum. Alternative sampling methods using Sebutape and Cup Scrubs can also be accommodated. Tape strip samples were placed in a 12 well plate under frozen conditions (−80° C.) until analysis. Tape samples were extracted for analysis by placing the tapes inside a polypropylene tube (2 ml) and adding extraction buffer (PBS, pH 7.4, 0.04% SDS, Protease Inhibitors) and sonicating for 30 min at 4° C. The samples were then centrifuged to remove any insoluble material and the supernatant is transferred into two deep well plates.

Supernatant samples for keratin analysis were fortified with 2.0% Bovine Serum Albumin (BSA) before freezing. The remaining supernatants were transferred to a second deep well plate for Soluble Protein analysis. Samples were analyzed for Skin analytes (Human Serum Albumin, keratin 1, 10, 11) using validated Millipore™ Multiplex immunoassay methods with a Bio-Plex Protein Array Reader system. Soluble protein determinations of the supernatants were performed using the Pierce BCA™ Protein assay kit with the aliquot designated for soluble protein using a validated method. The values obtained for soluble proteins were used to normalize. Skin analyte concentrations were reported as pg/mL or ng/mL and the soluble proteins were reported as µg/mL. Methods have been validated to demonstrate accuracy, precision, bench top stability, freeze thaw stability, short and long term storage stability of the extracts. Extration efficiency of the methods have been shown to be >70% and reproducible with a single extraction of the tape strips.

Quite surprisingly, the study showed that delivery of a rinse-off composition having a lipid to surfactant profile that varied over time provided measurable benefits well beyond the stage of high lipid delivery, as reported below.

Figure 16:
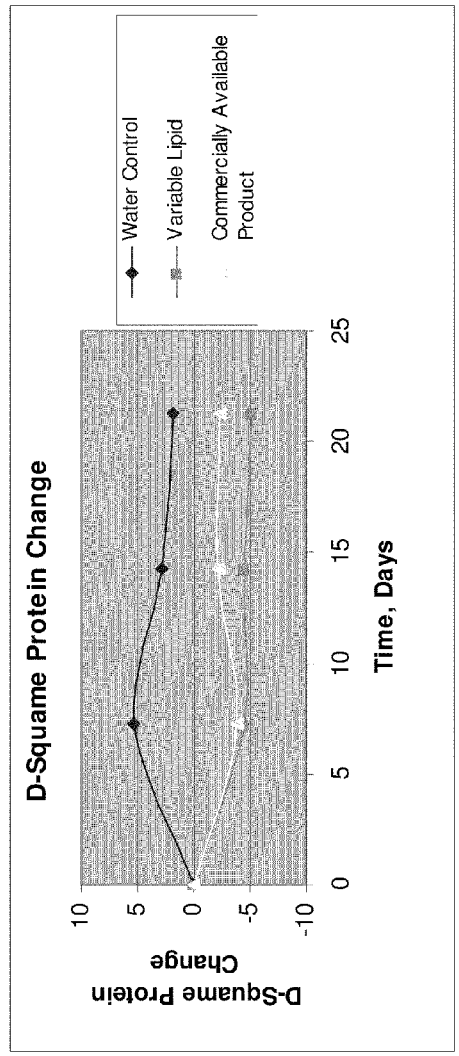
FIG. 16 shows the relative change in total protein using water, a personal care composition having a lathering phase to hydrophobic benefit phase ratio of 55:45 and a personal care composition having the lipid delivery profile as shown in FIG. 9.
Figure 17:
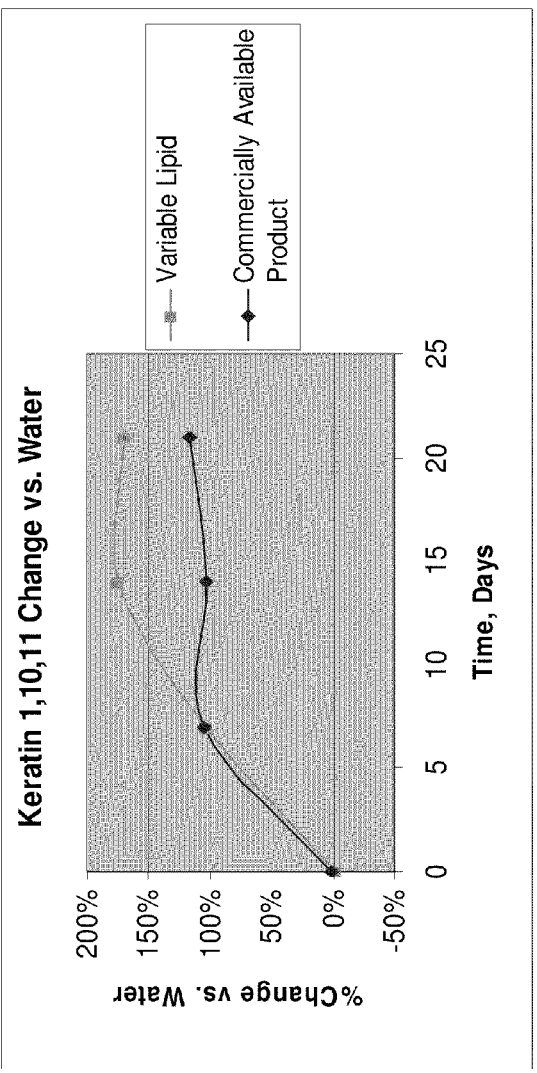
FIG. 17 shows the relative change in keratin 1, 10 and 11 normalized to soluble protein using water, a personal care composition having a lathering phase to hydrophobic benefit phase ratio of 55:45 and a personal care composition having the lipid delivery profile as shown in FIG. 9.

Total Protein Results: The results of the total protein from six consecutive tape strips as measured by SquameScan 850 were obtained. Referring to FIG. 16, comparative results according to the study are shown. The results showed improved cohesiveness at day 7.0, 14.0, and 22.0 measurement points vs. water control.

keratin 1, 10, 11 Results: The results of keratin 1, 10, 11 were normalized to total soluble protein. Referring to FIG. 17, comparative results according to the study are shown. A significant increase of normalized keratin 1, 10 11 as compared to water control at day 7 (100% increase) was observed. The normalized keratin 1, 10, 11 level is further increased to 150% vs. water at day 14 and 22. The data is consistent with literature reports that dry skin dry skin is a condition characterized by hyperproliferation and decreased differentiation. (See Engeke, Jensen, Ekanayake-Mudiyanselage and Proksch "Effects of xerosis and aging on epidermal proliferation and differentiation", Br. J. Dermatology, 137: 219-225 (1997).) This is the first known reported instance wherein measurable improvement in total keratin has been shown in the context of use of a rinse-off personal care composition.

Tables 10A-10I show detailed clinical results summary data, and include: Dryness, Corneometer, TEWL, total protein, Ue, Ur, Normalized keratin 1, 10, 11, non Normalized keratin 1, 10, 11, and Total Soluble Protein measurements.

TABLE 10A

EXPERT DRYNESS GRADES

| Attribute | Evaluation | Sample Size | Treatment | Statistical Grouping (95% confidence) | Adjusted Mean | Standard Error |
|---|---|---|---|---|---|---|
| Expert Dryness Grades | Day 1, Baseline | 53 | [A] Water | a | 2.794 | 0.054 |
| | | 53 | [B] Continuous Lipid | a | 2.813 | 0.054 |
| | | 53 | [C] Variable Lipid | a | 2.768 | 0.054 |
| Expert Dryness Grades | 24 Hr Post Wash 6 (7.0) | 51 | [A] Water | b | 2.417 | 0.103 |
| | | 53 | [B] Continuous Lipid | a | 2.062 | 0.101 |
| | | 51 | [C] Variable Lipid | a | 1.972 | 0.103 |
| Expert Dryness Grades | 24 Hr Post Wash 13 (14.0) | 48 | [A] Water | b | 2.781 | 0.103 |
| | | 50 | [B] Continuous Lipid | a | 2.355 | 0.102 |
| | | 48 | [C] Variable Lipid | a | 2.292 | 0.103 |
| Expert Dryness Grades | 24 Hr Post Wash 21 (22.0) | 46 | [A] Water | b | 2.804 | 0.113 |
| | | 49 | [B] Continuous Lipid | a | 2.564 | 0.111 |
| | | 47 | [C] Variable Lipid | a | 2.539 | 0.113 |

TABLE 10B

CORNEOMETER RESULTS

| | | Sample Size | Treatment | Statistical Grouping | Adjusted Mean | Standard Error |
|---|---|---|---|---|---|---|
| Corneometer | Day 1, Baseline | 53 | [A] Water | a | 20.936 | 0.690 |
| | | 53 | [B] Continuous Lipid | a | 20.935 | 0.690 |
| | | 53 | [C] Variable Lipid | a | 20.635 | 0.690 |
| Corneometer | 24 Hr Post Wash 6 (7.0) | 51 | [A] Water | a | 19.084 | 0.523 |
| | | 53 | [B] Continuous Lipid | b | 22.036 | 0.514 |
| | | 51 | [C] Variable Lipid | b | 22.720 | 0.523 |
| Corneometer | 24 Hr Post Wash 13 (14.0) | 48 | [A] Water | a | 18.102 | 0.559 |
| | | 50 | [B] Continuous Lipid | b | 20.204 | 0.550 |
| | | 48 | [C] Variable Lipid | bc | 20.604 | 0.558 |
| Corneometer | 24 Hr Post Wash 21 (22.0) | 46 | [A] Water | a | 17.513 | 0.493 |
| | | 49 | [B] Continuous Lipid | b | 19.275 | 0.480 |
| | | 47 | [C] Variable Lipid | b | 19.141 | 0.489 |

TABLE 10C

TEWL

| Attribute | Evaluation | Sample Size | Treatment | Statistical Grouping (95% confidence) | Adjusted Mean | Standard Error |
|---|---|---|---|---|---|---|
| TEWL Readings (Avg of 2 Probes) | Day 1, Baseline | 53 | [A] Water | a | 4.324 | 0.234 |
| | | 53 | [B] Continuous Lipid | a | 4.484 | 0.234 |
| | | 53 | [C] Variable Lipid | a | 4.370 | 0.234 |

TABLE 10C-continued

TEWL

| Attribute | Evaluation | Sample Size | Treatment | Statistical Grouping (95% confidence) | Adjusted Mean | Standard Error |
|---|---|---|---|---|---|---|
| TEWL Readings (Avg of 2 Probes) | 24 Hr Post Wash 6 (7.0) | 51 | [A] Water | bc | 5.108 | 0.201 |
| | | 53 | [B] Continuous Lipid | c | 5.217 | 0.199 |
| | | 51 | [C] Variable Lipid | abc | 4.991 | 0.201 |
| TEWL Readings (Avg of 2 Probes) | 24 Hr Post Wash 13 (14.0) | 48 | [A] Water | a | 6.092 | 0.190 |
| | | 50 | [B] Continuous Lipid | a | 6.149 | 0.188 |
| | | 48 | [C] Variable Lipid | a | 5.820 | 0.190 |
| TEWL Readings (Avg of 2 Probes) | 24 Hr Post Wash 21 (22.0) | 46 | [A] Water | a | 6.610 | 0.189 |
| | | 49 | [B] Continuous Lipid | a | 6.399 | 0.186 |
| | | 47 | [C] Variable Lipid | a | 6.301 | 0.188 |

TABLE 10D

TOTAL PROTEIN (SQUAMESCAN 850 UNIT)

| Attribute | Evaluation | Sample Size | Treatment | Statistical Grouping (95% confidence) | Adjusted Mean | Standard Error |
|---|---|---|---|---|---|---|
| Sum of First 6 Tape Strips | Day 1, Baseline | 53 | [A] Water | abc | 54.044 | 1.795 |
| | | 53 | [B] Continuous Lipid | ab | 53.328 | 1.795 |
| | | 53 | [C] Variable Lipid | c | 57.722 | 1.795 |
| Sum of First 6 Tape Strips | 24 Hr Post Wash 6 | 51 | [A] Water | c | 60.113 | 1.770 |
| | | 53 | [B] Continuous Lipid | ab | 50.874 | 1.743 |
| | | 51 | [C] Variable Lipid | a | 50.347 | 1.784 |
| Sum of First 6 Tape Strips | 24 Hr Post Wash 13 | 48 | [A] Water | bc | 57.452 | 1.766 |
| | | 50 | [B] Continuous Lipid | a | 52.495 | 1.739 |
| | | 48 | [C] Variable Lipid | a | 50.203 | 1.780 |
| Sum of First 6 Tape Strips | 24 Hr Post Wash 21 | 46 | [A] Water | c | 56.235 | 1.864 |
| | | 49 | [B] Continuous Lipid | ab | 52.024 | 1.828 |
| | | 47 | [C] Variable Lipid | a | 49.193 | 1.864 |

TABLE 10E

ELASTIC DEFORMATION (CUTOMETER RESULTS)

| Attribute | Evaluation | Sample Size | Treatment | Statistical Grouping (95% confidence) | Adjusted Mean | Standard Error |
|---|---|---|---|---|---|---|
| Ue - Elastic Deformation of Skin | Day 1, Baseline | 53 | [A] Water | a | 0.710 | 0.033 |
| | | 53 | [B] Continuous Lipid | a | 0.704 | 0.033 |
| | | 53 | [C] Variable Lipid | a | 0.669 | 0.033 |
| Ue - Elastic Deformation of Skin | 1 Hr Post Wash 14 (14.1) | 48 | [A] Water | a | 0.418 | 0.016 |
| | | 49 | [B] Continuous Lipid | b | 0.458 | 0.016 |
| | | 48 | [C] Variable Lipid | b | 0.472 | 0.016 |
| Ue - Elastic Deformation of Skin | 1 Hr Post Wash 21 (21.1) | 46 | [A] Water | a | 0.390 | 0.016 |
| | | 48 | [B] Continuous Lipid | b | 0.432 | 0.016 |
| | | 47 | [C] Variable Lipid | b | 0.421 | 0.016 |

TABLE 10F

ELASTIC RECOVERY (CORNEOMETER RESULTS)

| Attribute | Evaluation | Sample Size | Treatment | Statistical Grouping (95% confidence) | Adjusted Mean | Standard Error |
|---|---|---|---|---|---|---|
| Ur - Elastic Deformation Recovery | Day 1, Baseline | 53 | [A] Water | a | 0.665 | 0.029 |
| | | 53 | [B] Continuous Lipid | a | 0.647 | 0.029 |
| | | 53 | [C] Variable Lipid | a | 0.630 | 0.029 |
| Ur - Elastic Deformation Recovery | 1 Hr Post Wash 7 (7.1) | 50 | [A] Water | a | 0.432 | 0.020 |
| | | 52 | [B] Continuous Lipid | b | 0.470 | 0.019 |
| | | 50 | [C] Variable Lipid | b | 0.500 | 0.020 |
| Ur - Elastic Deformation Recovery | 1 Hr Post Wash 14 (14.1) | 48 | [A] Water | a | 0.401 | 0.018 |
| | | 49 | [B] Continuous Lipid | b | 0.446 | 0.018 |
| | | 48 | [C] Variable Lipid | b | 0.466 | 0.018 |
| Ur - Elastic Deformation Recovery | 1 Hr Post Wash 21 (21.1) | 46 | [A] Water | a | 0.378 | 0.018 |
| | | 48 | [B] Continuous Lipid | b | 0.441 | 0.018 |
| | | 47 | [C] Variable Lipid | b | 0.435 | 0.018 |

TABLE 10G

LOG(NORMALIZED KERATIN 1, 10, 11 TO SOLUBLE PROTEIN IN ng/ug)

| Attribute | Evaluation | Sample Size | Treatment | Statistical Grouping (95% confidence) | Adjusted Mean | Standard Error |
|---|---|---|---|---|---|---|
| Log(keratin 1, 10, 11 Ratio[Soluble Protein]) | Day 1, Baseline | 51 | [A] Water | a | 1.655 | 0.068 |
| | | 53 | [B] Continuous Lipid | a | 1.657 | 0.067 |
| | | 51 | [C] Variable Lipid | a | 1.642 | 0.068 |
| Log(keratin 1, 10, 11 Ratio[Soluble Protein]) | 24 Hr Post Wash 6 (7.0) | 51 | [A] Water | a | 1.730 | 0.072 |
| | | 53 | [B] Continuous Lipid | b | 2.040 | 0.071 |
| | | 51 | [C] Variable Lipid | b | 2.037 | 0.072 |
| Log(keratin 1, 10, 11 Ratio[Soluble Protein]) | 24 Hr Post Wash 13 (14.0) | 48 | [A] Water | a | 1.633 | 0.076 |
| | | 50 | [B] Continuous Lipid | bc | 1.942 | 0.074 |
| | | 48 | [C] Variable Lipid | c | 2.071 | 0.076 |
| Log(keratin 1, 10, 11 Ratio[Soluble Protein]) | 24 Hr Post Wash 21 (22.0) | 46 | [A] Water | a | 1.341 | 0.082 |
| | | 49 | [B] Continuous Lipid | b | 1.678 | 0.080 |
| | | 47 | [C] Variable Lipid | b | 1.771 | 0.081 |

TABLE 10H

Log (Non Normalized keratin 1, 10, 11 in ng/ml)

| Attribute | Evaluation | Sample Size | Treatment | Statistical Grouping (95% confidence) | Adjusted Mean | Standard Error |
|---|---|---|---|---|---|---|
| Log(keratin 1, 10, 11 No Normalization | Day 1, Baseline | 51 | [A] Water | ab | 3.806 | 0.057 |
| | | 53 | [B] Continuous Lipid | a | 3.741 | 0.057 |
| | | 51 | [C] Variable Lipid | ab | 3.794 | 0.057 |
| Log(keratin 1, 10, 11 No Normalization | 24 Hr Post Wash 6 (7.0) | 51 | [A] Water | b | 3.704 | 0.041 |
| | | 53 | [B] Continuous Lipid | ab | 3.645 | 0.040 |
| | | 51 | [C] Variable Lipid | a | 3.576 | 0.041 |
| Log(keratin 1, 10, 11 No Normalization | 24 Hr Post Wash 13 (14.0) | 48 | [A] Water | b | 3.750 | 0.057 |
| | | 50 | [B] Continuous Lipid | ab | 3.617 | 0.056 |
| | | 48 | [C] Variable Lipid | a | 3.606 | 0.057 |

TABLE 10H-continued

Log (Non Normalized keratin 1, 10, 11 in ng/ml)

| Attribute | Evaluation | Sample Size | Treatment | Statistical Grouping (95% confidence) | Adjusted Mean | Standard Error |
|---|---|---|---|---|---|---|
| Log(keratin 1, 10, 11 No Normalization | 24 Hr Post Wash 21 (22.0) | 46 | [A] Water | c | 3.785 | 0.054 |
| | | 49 | [B] Continuous Lipid | bc | 3.726 | 0.052 |
| | | 47 | [C] Variable Lipid | ab | 3.644 | 0.053 |

TABLE 10I

LOG(SOLUBLE PROTEIN IN ug/ml)

| Attribute | Evaluation | Sample Size | Treatment | Statistical Grouping (95% confidence) | Adjusted Mean | Standard Error |
|---|---|---|---|---|---|---|
| Log(Soluble Protein) | Day 1, Baseline | 51 | [A] Water | a | 2.150 | 0.072 |
| | | 53 | [B] Continuous Lipid | a | 2.085 | 0.071 |
| | | 51 | [C] Variable Lipid | a | 2.155 | 0.072 |
| Log(Soluble Protein) | 24 Hr Post Wash 6 (7.0) | 51 | [A] Water | b | 1.971 | 0.081 |
| | | 53 | [B] Continuous Lipid | a | 1.605 | 0.080 |
| | | 51 | [C] Variable Lipid | a | 1.542 | 0.081 |
| Log(Soluble Protein) | 24 Hr Post Wash 13 (14.0) | 48 | [A] Water | b | 2.119 | 0.084 |
| | | 50 | [B] Continuous Lipid | a | 1.672 | 0.083 |
| | | 48 | [C] Variable Lipid | a | 1.535 | 0.084 |
| Log(Soluble Protein) | 24 Hr Post Wash 21 (22.0) | 46 | [A] Water | c | 2.446 | 0.089 |
| | | 49 | [B] Continuous Lipid | b | 2.040 | 0.088 |
| | | 47 | [C] Variable Lipid | ab | 1.884 | 0.089 |

Figure 18:
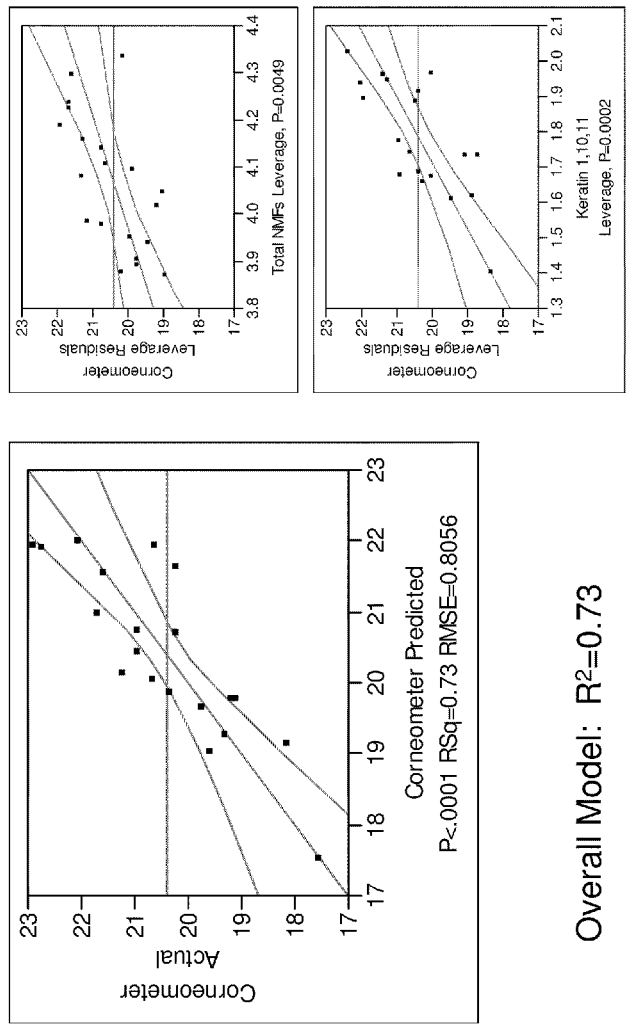
FIG. 18 shows plots of objective physical measurement of corneometer improvement as a function of combined biomarker measurements.
Figure 19:
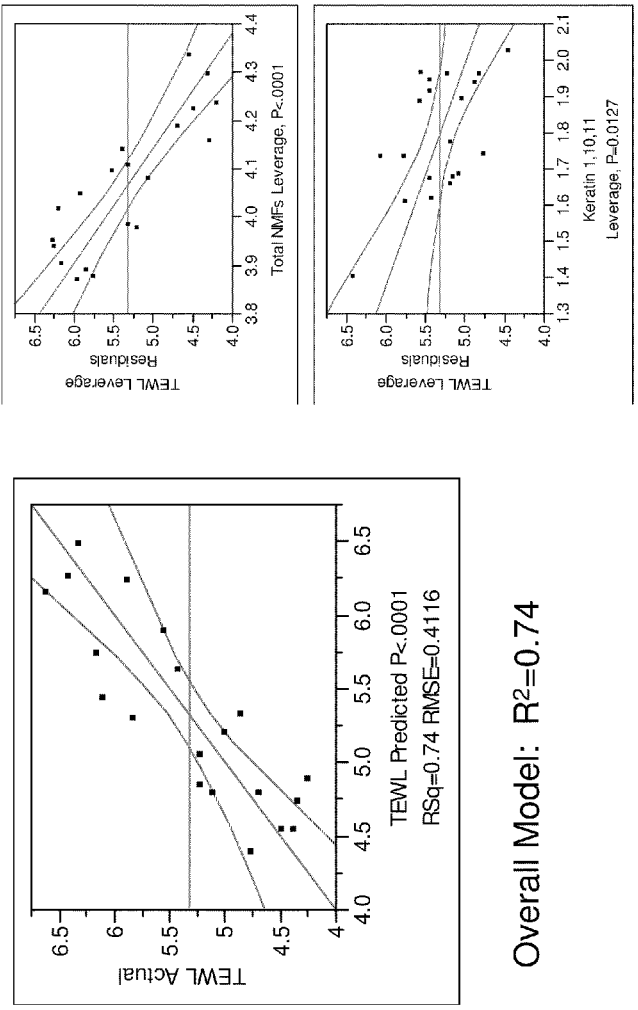
FIG. 19 shows plots of objective physical measurement of trans-epidermal water loss improvement as a function of combined biomarker measurements.
Figure 21A:
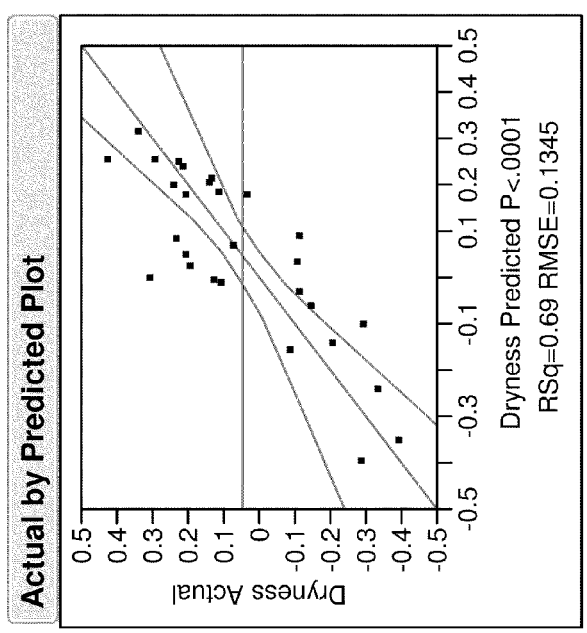
FIG. 21A shows plots of predictability of skin dryness as a function of combined biomarkers including log IL 1ra/1α, NMF, and total protein biomarker measurements.
Figure 21B:
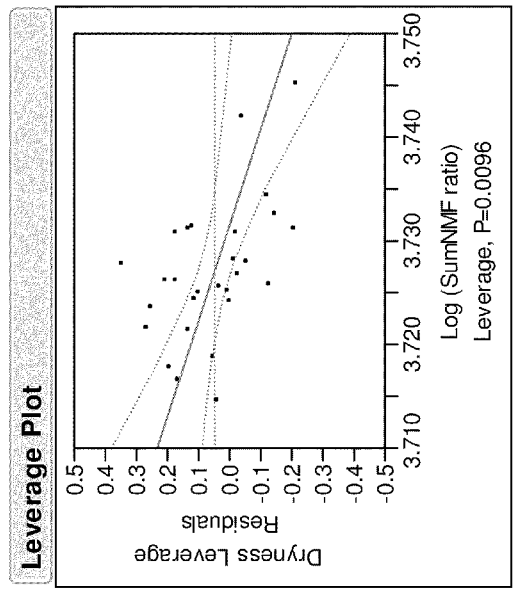
FIG. 21B shows plots of dryness improvement as a function of inflammatory NMF.
Figure 21C:
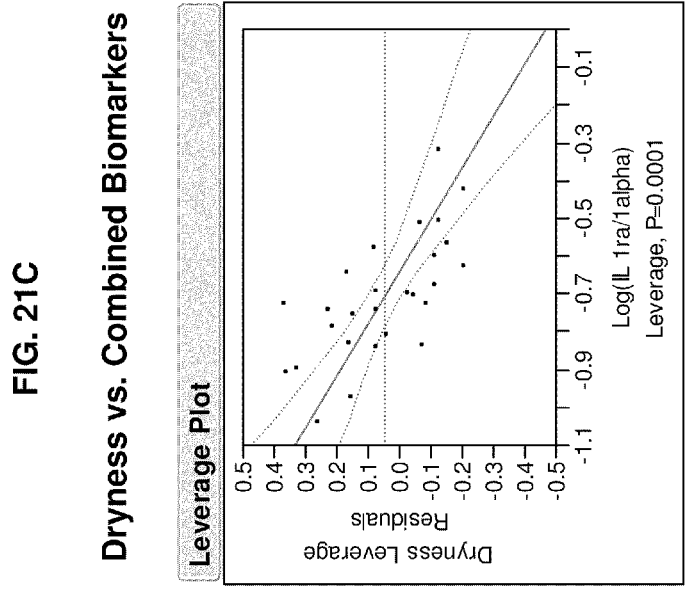
FIG. 21C shows plots of dryness improvement as a function of inflammatory cytokines (log IL 1ra/1α).
Figure 21D:
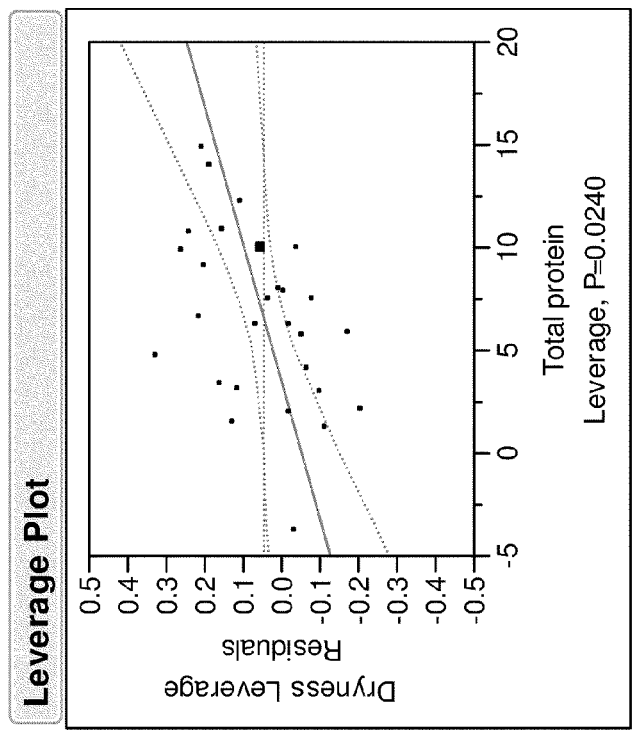
FIG. 21D shows plots of dryness improvement as a function of total protein.

Based on the results as reported above, further analysis of the results was undertaken to determine whether the measured skin health correlates with the biomarker measurements as obtained in the study. The results are reported in FIGS. 18 through 21. Referring to FIG. 18 and FIG. 19, it is evident that the combined biomarkers keratin 1, 10, 11 are key indicators for skin dryness and corneometer hydration, and the measured increases in these biomarkers trend well with objective measures of improvement in skin dryness and hydration. Referring again to FIG. 19 and FIG. 20, the analysis shows that total NMFs are key indicators for TEWL and elastic recovery (Ur), and the measured increases in these biomarkers trend well with objective measures of improvement retention of moisture and elasticity. More generally, as shown in FIG. 18 and FIG. 21, the inflammatory cytokines, NMFs, keratins and total protein measured increases all are predictive of physical improvements.

These results are the first known report of measurement of biomarkers for demonstrating improvement of skin as shown by objective measures. We have demonstrated that use of the biomarker panels as described herein supports the formulation of personal care products, particularly in the rinse-off context, that achieve objective improvement of skin health. In addition, the methods described herein enable the identification and hence the formulation of products that can deliver sustained benefits beyond the treatment period.

Example 3: Calculation of Improvement Indices for Physical Measurements and Biomarkers The above described results indicate that the variable lipid body wash delivers significant improvements in several standard moisturization/tissue health measures (dryness grades, corneometer hydration, and TEWL). We believe we are the first to report in the rinse-off context, the results show significant improvement in skin elasticity as compared to the water treatment control. The total protein results further reveal significant improvement in stratum corneum cohesiveness. Taken together, these findings support the conclusion that the petrolatum depositing body wash wherein hydrophobic benefit phase is delivered in varying amounts over a treatment cycle according various embodiments as described herein improves the overall condition of skin. Improvement indices for each of the measures described herein above are shown in Table 11A and B.

TABLE 11A

| Improvement Index | Inventive Example A vs. Water Control | p value (base size n = 50) |
|---|---|---|
| a) Skin Elastic Extension (Ue) Improvement Index | 16 | p = 0.003 |
| b) Skin Elastic Recovery (Ur) Improvement Index | 21 | p = 0.0004 |
| c) Skin Elasticity (R7) Improvement Index | 4 | p = 0.05 |
| d) Stratum Corneum Cohesiveness Improvement Index | 23 | p < 0.0001 |
| e) keratin Improvement Index | 172 | p < 0.0001 |
| f) Visual Dryness Improvement (Dryness Reduction at 3 hours after three weeks of product treatment) | 1.5 | p < 0.0001 |

TABLE 11A-continued

| Improvement Index | Inventive Example A vs. Water Control | p value (base size n = 50) |
|---|---|---|
| g) Corneometer Improvement (Increase in Corneometer at 3 hours after three weeks of product treatment) | 3.6 | p < 0.0001 |
| h) TEWL Improvement (TEWL reduction at 3 hours after three weeks of product treatment) | 0.5 | P = 0.016 |

TABLE 11B

| Improvement Index | Inventive Example A vs. Water Control | p value (base size n = 50) |
|---|---|---|
| a) Inflammatory Cytokines | 113 | P < 0.0001 |
| b) NMFs | 5.7 | p = 0.0737 |
| c) Ceramides | 57 | p = 0.0008 |
| d) Fatty Acids | 43 | p = 0.0015 |
| e) Total protein | 8.2 | P = 0.0002 |

Calculation Improvement Index

1) Calculation of Skin Elasticity Improvement Index a) Elastic Extension ($U_e$) Improvement Index is calculated as:

$$[(U_e)^P_{end} - (U_e)^c_{end}]/(U_e)^c_{end} * 100 - [(U_e)^P_{ini} - (U_e)^c_{ini}]/(U_e)^c_{ini} * 100 \text{ wherein}$$

$(U_e)^c_{ini}$ is the initial elastic extension parameter at the beginning of the water control leg;

$(U_e)^P_{ini}$ is the initial elastic extension parameter at the beginning of the test product leg;

$(U_e)^c_{end}$ is the final elastic extension parameter at the end of the water control leg;

$(U_e)^P_{end}$ is the final elastic extension parameter at the end of the test product leg.

b) Elastic Recovery ($U_r$) Improvement Index is calculated as:

$$[(U_r)^P_{end} - (U_r)^c_{end}]/(U_r)^c_{end} * 100 - [(U_r)^P_{ini} - (U_r)^c_{ini}]/(U_r)^c_{ini} * 100 \text{ wherein}$$

$(U_r)^c_{ini}$ is the initial elastic recovery parameter at the beginning of the water control leg;

$(U_r)^P_{ini}$ is the initial elastic recovery at the beginning of the test product leg;

$(U_r)^c_{end}$ is the final elastic recovery at the end of the water control leg;

$(U_r)^P_{end}$ is the final elastic recovery at the end of the test product leg.

c) Elasticity ($R_7$) Improvement Index is calculated as:

$$[(R_7)^P_{end} - (R_7)^c_{end}]/(R_7)^c_{end} * 100 - [(R_7)^P_{ini} - (R_7)^c_{ini}]/(R_7)^c_{ini} * 100 \text{ wherein}$$

$(R_7)^c_{ini}$ is the initial elasticity at the beginning of the water control leg;

$(R_7)^P_{ini}$ is the initial elasticity at the beginning of the test product leg;

$(R_{7r})^c_{end}$ is the final elasticity at the end of the water control leg;

$(R_7)^P_{end}$ is the final elasticity at the end of the test product leg.

2) Calculation of Stratum Corneum Cohesiveness Improvement Index

Stratum Corneum Cohesiveness Improvement Index is calculated as:

$$[(\text{Protein})^C_{end} - (\text{Protein})^P_{end}]/(\text{Protein})^C_{end} * 100 - [(\text{Protein})^C_{ini} - (\text{Protein})^P_{ini}]/(\text{Protein})^C_{ini} * 100$$
wherein $(\text{Protein})^c_{ini}$ is the sum of initial protein absorption of tape 1 to tape 6 at the beginning of the water control leg;

$(\text{Protein}_e)^P_{ini}$ is the sum of initial protein absorption of tape 1 to tape 6 at the beginning of the test product leg;

$(\text{Protein})^c_{end}$ is the sum of final protein absorption of tape 1 to tape 6 at the end of the water control leg;

$(\text{Protein})^P_{end}$ is the sum of final protein absorption of tape 1 to tape 6 at the end of the test product leg.

3) Calculation of Keratin 1, 10, 11 Improvement Index

Keratin 1, 10, 11 Improvement Index is calculated as:

$$[(\text{keratin})^P_{end} - (\text{keratin})^C_{end}]/(\text{keratin})^C_{end} * 100 - [(\text{keratin})^P_{ini} - (\text{keratin})^C_{ini}]/(\text{keratin})^C_{ini} * 100$$
wherein $(\text{keratin})^c_{ini}$ is the initial keratin 1, 10, 11 normalized to total soluble protein at the beginning of the water control leg;

$(\text{keratin})^P_{ini}$ is the initial keratin 1, 10, 11 normalized to total soluble protein at the beginning of the test product leg;

$(\text{keratin})^c_{end}$ is the final keratin 1, 10, 11 normalized to total soluble protein at the end of the water control leg;

$(\text{keratin})^P_{end}$ is the final keratin 1, 10, 11 normalized to total soluble protein at end of the test product leg.

4) Calculation of Inflammatory Cytokine Improvement Index

Cytokine Improvement Index is calculated as:

$$[(\text{Cytokine})^c_{end} - (\text{Cytokine})^P_{end}]/(\text{Cytokine})^C_{end} * 100 - [(\text{Cytokine})^c_{ini} - (\text{Cytokine})^P_{ini}]/(\text{Cytokine})^C_{ini} * 100 \text{ wherein}$$

$(\text{Cytokine})^c_{ini}$ is the initial Cytokine normalized to total soluble protein at the beginning of the water control leg;

$(\text{Cytokine})^P_{ini}$ is the initial Cytokine normalized to total soluble protein at the beginning of the test product leg;

$(\text{Cytokine})^c_{end}$ is the final Cytokine normalized to total soluble protein at the end of the water control leg;

$(\text{Cytokine})^P_{end}$ is the final Cytokine normalized to total soluble protein at end of the test product leg.

5) Calculation of NMF Improvement Index

NMF Improvement Index is calculated as:

$$[(\text{NMF})^P_{end} - (\text{NMF})^c_{end}]/(\text{NMF})^C_{end} * 100 - [(\text{NMF})^P_{ini} - (\text{NMF})^c_{ini}]/(\text{NMF})^C_{ini} * 100 \text{ wherein}$$

$(\text{NMF})^c_{ini}$ is the initial NMF normalized to total soluble protein at the beginning of the water control leg;

$(\text{NMF})^P_{ini}$ is the initial NMF normalized to total soluble protein at the beginning of the test product leg;

$(\text{NMF})^c_{end}$ is the final NMF normalized to total soluble protein at the end of the water control leg;

$(\text{NMF})^P_{end}$ is the final NMF normalized to total soluble protein at end of the test product leg.

6) Calculation of Ceramides Improvement Index

Ceramides Improvement Index is calculated as:

$$[(\text{Ceramides})^P_{end} - (\text{Ceramides})^c_{end}]/(\text{Ceramides})^C_{end} * 100 - [(\text{Ceramides})^P_{ini} - (\text{Ceramides})^c_{ini}]/(\text{Ceramides})^C_{ini} * 100 \text{ wherein}$$

$(\text{Ceramides})^c_{ini}$ is the initial Ceramides normalized to total soluble protein at the beginning of the water control leg;

$(\text{Ceramides})^P_{ini}$ is the initial Ceramides normalized to total soluble protein at the beginning of the test product leg;

(Ceramides)$^c_{end}$ is the final Ceramides normalized to total soluble protein at the end of the water control leg;

(Ceramides)$^P_{end}$ is the final Ceramides normalized to total soluble protein at the end of the test product leg.

7) Calculation of Fatty Acids Improvement Index

Fatty Acids Improvement Index is calculated as:

[(Fatty Acids)$^P_{end}$−(Fatty Acids)$^c_{end}$]/(Fatty Acids)$^C_{end}$*100−[(Fatty Acids)$^P_{ini}$−(Fatty Acids)$^c_{ini}$]/(Fatty Acids)$^C_{ini}$*100 wherein (Fatty Acids)$^c_{ini}$ is the initial Fatty Acids normalized to total soluble protein at the beginning of the water control leg;

(Fatty Acids)$^P_{ini}$ is the initial Fatty Acids normalized to total soluble protein at the beginning of the test product leg;

(Fatty Acids)$^c_{end}$ is the final Fatty Acids normalized to total soluble protein at the end of the water control leg;

(Fatty Acids)$^P_{end}$ is the final Fatty Acids normalized to total soluble protein at end of the test product leg.

8) Calculation of Total Protein Improvement Index

Cytokine Improvement Index is calculated as:

[(Total Protein)$^c_{end}$−(Total Protein)$^P_{end}$]/(Total Protein)$^C_{end}$*100−[(Total Protein)$^c_{ini}$−(Total Protein)$^P_{ini}$]/(Total Protein)$^C_{ini}$*100 wherein (Total Protein)$^c_{ini}$ is the initial Total Protein at the beginning of the water control leg;

(Total Protein)$^P_{ini}$ is the initial Total Protein at the beginning of the test product leg;

(Total Protein)$^c_{end}$ is the final Total Protein at the end of the water control leg;

(Total Protein)$^P_{end}$ is the final Total Protein at end of the test product leg.

Example 4: Biomarker Assay Methods

Cytokine, SkinMAP and Soluble Protein: Samples are collected for Biomarker analysis using D-Squame Tape Strips. D-Squame tapes are applied on the site of interest (Scalp, Leg, Face, Underarm, Forearm) with constant pressure/time, and removed to collect samples of the stratum corneum. Alternative sampling methods using Sebutape and Cup Scrubs can also be accommodated. Tape strip samples are placed in a 12 well plate under frozen conditions (−80° C.) until analysis. Tape samples are extracted for analysis by placing the tapes inside a polypropylene tube (2 ml) and adding extraction buffer (PBS, pH 7.4, 0.04% SDS, Protease Inhibitors) and sonicating for 30 min at 4° C. The samples are then centrifuged to remove any insoluble material and the supernatant is transferred into two deep well plates. Supernatant samples for Cytokine/SkinMAP analysis are fortified with 2.0% Bovine Serum Albumin (BSA) before freezing. The remaining supernatants are transferred to a second deep well plate for Soluble Protein analysis. Samples are analyzed for Cytokines (IL-1α, IL-1ra, IL-8) and Skin analytes (Human Serum Albumin, keratin 1, 10, 11 and Involucrin) using validated Millipore™ Multiplex immunoassay methods with a Bio-Plex Protein Array Reader system. Soluble protein determinations of the supernatants are performed using the Pierce BCA™ Protein assay kit with the aliquot designated for soluble protein using a validated method. The values obtained for soluble proteins are used to normalize the Cytokine and Skin Map data. Cytokine and Skin analyte concentrations are reported as pg/mL or ng/mL and the soluble proteins are reported as μg/mL. Methods have been validated to demonstrate accuracy, precision, bench top stability, freeze thaw stability, short and long term storage stability of the extracts. Extraction efficiency of the methods have been shown to be >70% and reproducible with a single extraction of the tape strips.

Lipids: Samples for lipid analysis are collected using D-Squame tapes similar to protein biomarker analysis. The samples are extracted using a solution (400 mM Urea and 2.0% SDS) with tapes suspended in this solution in scintillation vials. The tapes are sonicated and the extract suspension is removed to a separate scintillation vial for lipid extraction. Chloroform/Methanol is added according to the method with stable label internal standards for lipid extraction. The organic layer containing the lipids are removed and dried for analysis of lipids by SFC-HPLC/MS/MS. Total protein (soluble and insoluble) in the tape extracts were determined using BCA™ (Pierce) method.

Example 5: Dryness Grading Procedure

The skin on the subject's lower leg will be graded for dryness by a qualified grader according to the scales below. Each subject's lower legs will be visually evaluated at baseline on Study Day 8 (prior to product application), as a prerequisite for continuation into the treatment phase. Only those subjects with baseline dryness scores ≥2.5 and <4.0 on the scale below on each of the defined sites will qualify for enrollment into the treatment phase of the study. Each site on the subject's legs will be graded 9 more times: 3 hours post $1^{st}$, $3^{rd}$ $5^{th}$ $14^{th}$ and $21^{st}$ treatments; 24 hours post $4^{th}$, $13^{th}$ and $21^{st}$, treatments, 48 hours post $21^{st}$ treatment. Subjects will acclimate for a minimum of thirty minutes in an environmentally controlled room (maintained at 70° F.±2 and 30-45% relative humidity) prior any visual evaluations of their legs. The same skin grader will be used for the duration of the study. Data will be recorded electronically using the Sponsor's direct data entry and data capture programs.

If a termination score is suspected, the Investigator will arrange to have the subject's legs evaluated by a qualified Grader between three and four hours (if possible) after the previous treatment. If necessary, the subject will be asked to return to the test facility at a later time for this visual evaluation. If the Grader determines that the subject has attained dryness grade ≥5.0 on any site the subject will be dropped and a Subject Drop Form (DCF DROP) will be completed. The scores assigned to the sites at the time of the drop will be considered the final evaluation scores. Final instrumental measurements will also be made at this time. These visual and instrumental results will be included in the study data set. If the Investigator deems that the irritation does not interfere with the adjacent sites and there is no other reason for withdrawal, the subject's participation in the study will not be discontinued and treatment and evaluations of the remaining sites will be continued until the end of the study.

Materials: Visual evaluations will be done with the aid of a Luxo Illuminated Magnifying Lamp (Model KFM-1A) which provides 2.75× magnification and which has a shadow-free circular fluorescent light source (General Electric Cool White, 22 watt 8" Circline bulb).

| Grade[a] | Dryness[b] |
|---|---|
| 0.0 | perfect skin |
| 1.0 | patches of checking and/or slight powderiness, occasional patches of small scales may be seen, distribution generalized |
| 2.0 | generalized slight powderiness, early cracking or occasional small lifting scales may be present |

-continued

| Grade[a] | Dryness[b] |
|---|---|
| 3.0 | generalized moderate powderiness and/or moderate cracking and scales |
| 4.0 | generalized heavy powderiness and/or heavy cracking and lifting scales |
| 5.0 | generalized high cracking and lifting scales, eczematous change may be present but not prominent, may see bleeding cracks |
| 6.0 | generalized severe cracking, bleeding cracks and eczematous changes may be present, large scales may be sloughing off |

[a]half-unit grades may be used if necessary
[b]'generalized' refers to situations where more than 50% of the application area is affected Example 6: Corneometer Measurements Measurement Procedure: Skin hydration based upon the measurement of capacitance will be assessed using the Corneometer® 825. These non-invasive measurements will be taken in duplicate on each site of the subjects' legs a total of 10 times: at baseline, prior to $1^{st}$ treatment; 3 hours post $1^{st}$, $3^{rd}$, $5^{th}$ $14^{th}$ and $21^{st}$ treatments; 24 hours post $4^{th}$, $13^{th}$ and $21^{st}$, treatments, 48 hours post $21^{st}$ treatment after the visual assessment have been completed. Subjects will acclimate for a minimum of thirty minutes in an environmentally controlled room (maintained at 70° F.±2 and 30-45% relative humidity) prior to non-invasive instrumental measurements taken on their legs. Data will be recorded electronically using the Sponsor's direct data entry and data capture programs.

Operating Instructions: The taking of these measurements will be done according to the test facility's SOP's and/or the Sponsors Instrument Operation Manual.

1) The Corneometer values are arbitrary units for electrical impedance. At baseline these values typically fall within a similar range. If a measurement is outside of this observed range re-take the measurement following the procedure in the Sponsor's Instrument Operational Manual. If the value continues to be outside of the observed range then the study coordinator will contact the Clinical Trial Manager to determine if further action is needed. The values along with the subject # and visit are to be recorded on an error log sheet. Post-treatment measurements will also typically result in values within a similar range depending on the treatment. Post-treatment measurements outside this range will also be re-checked and recorded as above.
2) The instrument will be operated by only trained operators. Training record must be on file and up to date. The same instrument(s) and operator(s) will be used throughout the study.
3) Only use Kimwipes to wipe the end of the probe. The probe should be wiped with a Kimwipe between each measurement.
4) At the end of the evaluation session back up the data collected for that period following the instructions in the Sponsors Instrument Operation Manual. In addition you will print a hard copy of the data collected for the period.

Example 7: TEWL Measurements

Measurement Procedure: The integrity of the stratum corneum barrier will be assessed by transepidermal water loss using the DermaLab® Evaporimeter equipped with dual probes. Single non-invasive measurements will be taken on each site of the subjects' lower leg a total of 9 times: at baseline, prior to $1^{st}$ treatment; 3 hours post $3^{rd}$, $5^{th}$ $14^{th}$ and $21^{st}$ treatments; 24 hours post $4^{th}$, $13^{th}$ and $21^{st}$, treatments, 48 hours post $21^{st}$ treatment after the visual assessment and instrumental measurements have been completed. Due to the number of subjects and the time involved two instruments will be used during the study. Subjects will be assigned to one of the two instruments on the basis of their assigned subject number for the duration of the study. Each measurement consists of readings collected for 60 seconds with the mean of the last 20 seconds recorded from both probes (Channel A and Channel B). Subjects will acclimate for a minimum of thirty minutes in an environmentally controlled room (maintained at 70° F.±2 and 30-45% relative humidity) prior to instrumental measurements. Data will be recorded electronically using the Sponsor's data capture programs.

Operating Instructions: The taking of these measurements will be done according to the test facility's SOP's and/or the Sponsors Instrument Operation Manual.

1) The DermaLab values are arbitrary units of transepidermal water loss from the skin. At baseline these values typically fall within a similar range. If a measurement is outside of this observed range re-take the measurement following the procedure in the Sponsor's Instrument Operational Manual. If the value continues to be outside of the observed range then the study coordinator will contact the Clinical Trial Manager to determine if further action is needed. The values along with the subject # and visit are to be recorded on an error log sheet. Post-treatment measurements will also typically result in values within a similar range depending on the treatment. Post-treatment measurements outside this range will also be re-checked and recorded as above.
2) If one of the two probes fails during any measurement phase all subsequent measurements will be taken with the remaining single probe.
3) The instrument(s) will be operated by only trained operators. Training record must be on file and up to date. The same instrument(s) and operator(s) will be used throughout the study.
4) Only use Kimwipes to wipe the end of the probe. The probe should be wiped with a Kimwipe between each measurement.
5) At the end of the evaluation session back up the data collected for that period following the instructions in the Sponsors Instrument Operation Manual. In addition you will print a hard copy of the data collected for the period.

All percentages, parts and ratios are based upon the total weight of the compositions used in accordance with the present disclosure, unless otherwise specified. All such weights as they pertain to listed ingredients are based on the active level and, therefore; do not include solvents or by-products that may be included in commercially available materials, unless otherwise specified. The term "weight percent" may be denoted as "wt. %" herein. Except where specific examples of actual measured values are presented, numerical values referred to herein should be considered to be qualified by the word "about."

All molecular weights as used herein are weight average molecular weights expressed as grams/mole, unless otherwise specified.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm"

All documents cited in the Detailed Description are, in relevant part, incorporated herein by reference; the citation of any document is not to be construed as an admission that it is prior art with respect to the present disclosure. To the extent that any meaning or definition of a term in this document conflicts with any meaning or definition of the same term in a document incorporated by reference, the meaning or definition assigned to that term in this document shall govern.

While particular embodiments as disclosed herein have been illustrated and described, it would be obvious to those skilled in the art that various other changes and modifications can be made without departing from the spirit and scope of the disclosure. It is therefore intended to cover in the appended claims all such changes and modifications that are within the scope of this disclosure.

What is claimed is:

1. A method of identifying a rinse off personal care composition as effective for improving the stratum corneum barrier in a human subject who is a member of a selected population of subjects, comprising:
   (a) generating one or more control skin profiles for two or more subjects in a select population of subjects wherein the subjects in the select population have dry or damaged skin;
   (b) contacting at least a portion of skin of the subjects with a rinse-off test composition, rinsing the test composition off the portion of skin, extracting one or more skin samples from each of the subjects, and generating from the extracted samples one or more test profiles for the subjects;
   (c) comparing the one or more test profiles to the one or more control profiles and identifying the rinse-off test composition as effective for improving the stratum corneum barrier in a human subject who is a member of a selected population of subjects if the test profile is directionally shifted away from the control profile and shows (i) a decrease in one or more inflammatory cytokines, (ii) an increase in one or more natural moisturizing factors, (iii) an increase in one or more lipids, and (iv) a decrease in total protein.

2. The method according to claim 1, further comprising the step of comparing the one or more test profiles to the one or more control profiles and identifying the proposed formulation as effective if the test profile is directionally shifted away from the control profile and shows at least one of the following biomarker changes (i) an increase in one or more of keratin 1, keratin 10 and keratin.

3. The method according to any one of the preceding claims, wherein the steps are repeated for a different target population.

4. The method according to claim 1, wherein the one or more inflammatory cytokines are selected from IL1rα and IL 1α, the one or more natural moisturizing factors are selected from amino acids, lactic acid, urea, and pyrrolidone carboxylic acid, and the one or more lipids are selected from one or more ceramides selected from NP-C18, NP-C23, NP-C26, NP-C28, NP-C30, AP-C24, AP-C26, AH-C24, AH-C26, NdS-C24, NdS-C26, EOS-C30.

5. The method according to claim 4, wherein the decrease in one or more inflammatory cytokines is evidenced by an inflammatory cytokine improvement index from 5 to 2000, the increase in one or more natural moisturizing factors is evidenced by an NMF improvement index from −1.0 to 25, the increase in one or more of keratin 1, keratin 10 and keratin 11 is evidenced by a keratin improvement index from 20 to 1000, and the increase in one or more lipids is evidenced by an lipid improvement index for ceramides from 5 to 500, an lipid improvement index for fatty acids from 5 to 400.

6. The method according to claim 1, wherein the decrease in total protein is evidenced by total protein improvement index from 5 to 50.

* * * * *